United States Patent
Takekoshi

(10) Patent No.: US 11,832,021 B2
(45) Date of Patent: Nov. 28, 2023

(54) CONTROL APPARATUS, CONTROL METHOD, AND STORAGE MEDIUM

(71) Applicant: CANON KABUSHIKI KAISHA, Tokyo (JP)

(72) Inventor: Koji Takekoshi, Fujisawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/840,517

(22) Filed: Jun. 14, 2022

(65) Prior Publication Data
US 2022/0321800 A1    Oct. 6, 2022

Related U.S. Application Data

(63) Continuation of application No. 16/122,686, filed on Sep. 5, 2018, now Pat. No. 11,388,353, which is a
(Continued)

(30) Foreign Application Priority Data
Jan. 30, 2015    (JP) ................ 2015-017888

(51) Int. Cl.
| | |
|---|---|
| *G01T 1/24* | (2006.01) |
| *G06F 3/14* | (2006.01) |
| *H04N 5/265* | (2006.01) |
| *A61B 6/00* | (2006.01) |
| *G06T 7/90* | (2017.01) |
| *H04N 23/90* | (2023.01) |
| *H04N 23/63* | (2023.01) |

(Continued)

(52) U.S. Cl.
CPC .......... *H04N 5/265* (2013.01); *A61B 6/4266* (2013.01); *A61B 6/465* (2013.01); *A61B 6/5241* (2013.01); *A61B 6/54* (2013.01); *A61B 6/56* (2013.01); *G06T 7/0012* (2013.01); *G06T 7/90* (2017.01); *H04N 23/631* (2023.01); *H04N 23/667* (2023.01); *H04N 23/90* (2023.01); *A61B 6/4283* (2013.01); *G06T 2207/30004* (2013.01); *G06T 2207/30196* (2013.01)

(58) Field of Classification Search
CPC .... H04N 5/265; H04N 23/631; H04N 23/667; H04N 23/90; H04N 5/2624; H04N 23/62; A61B 6/4266; A61B 6/465; A61B 6/5241; A61B 6/54; A61B 6/56; A61B 6/4283; A61B 6/4411; A61B 6/40; A61B 6/548; A61B 6/4208; G06T 7/0012; G06T 7/90; G06T 2207/30004; G06T 2207/30196
See application file for complete search history.

(56) References Cited

U.S. PATENT DOCUMENTS

| | | | |
|---|---|---|---|
| 11,388,353 B2 * | 7/2022 | Takekoshi | ............ G06T 7/90 |
| 2014/0321614 A1 | 10/2014 | Yamada | |

(Continued)

FOREIGN PATENT DOCUMENTS

CN    102379708 A    3/2012

*Primary Examiner* — Howard D Brown, Jr.
(74) *Attorney, Agent, or Firm* — CANON U.S.A., INC. IP Division

(57) ABSTRACT

A control apparatus for stitch imaging makes a first determination, or a second determination, and a display control unit configured to control a display of a display unit according to whether the determination made by the determination unit is the first determination or the second determination.

18 Claims, 15 Drawing Sheets

Related U.S. Application Data continuation of application No. 15/008,988, filed on Jan. 28, 2016, now Pat. No. 10,104,311.

(51) Int. Cl.
*H04N 23/667* (2023.01)
*G06T 7/00* (2017.01)

(56) References Cited

U.S. PATENT DOCUMENTS

| | | | |
|---|---|---|---|
| 2016/0227130 A1* | 8/2016 | Takekoshi | H04N 23/631 |
| 2016/0302753 A1* | 10/2016 | Suzuki | A61B 6/5241 |
| 2018/0055465 A1* | 3/2018 | Nakayama | A61B 6/4452 |
| 2019/0007627 A1* | 1/2019 | Takekoshi | H04N 23/631 |
| 2019/0110376 A1* | 4/2019 | Tagawa | G01T 1/244 |
| 2020/0396395 A1* | 12/2020 | Kuwata | H04N 23/661 |
| 2022/0125399 A1* | 4/2022 | Tanno | G06F 3/14 |
| 2023/0041440 A1* | 2/2023 | Kim | A61B 5/448 |

* cited by examiner

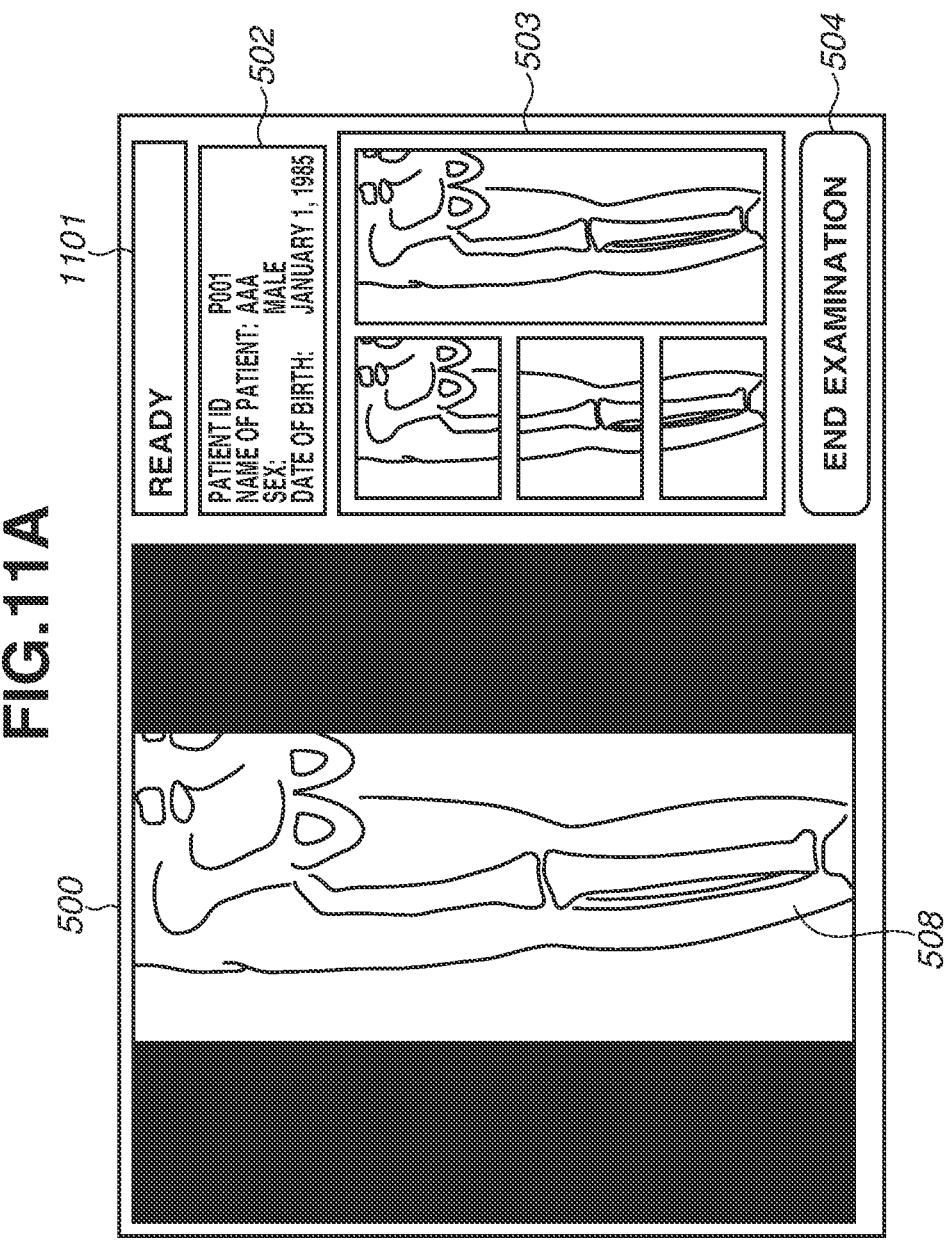

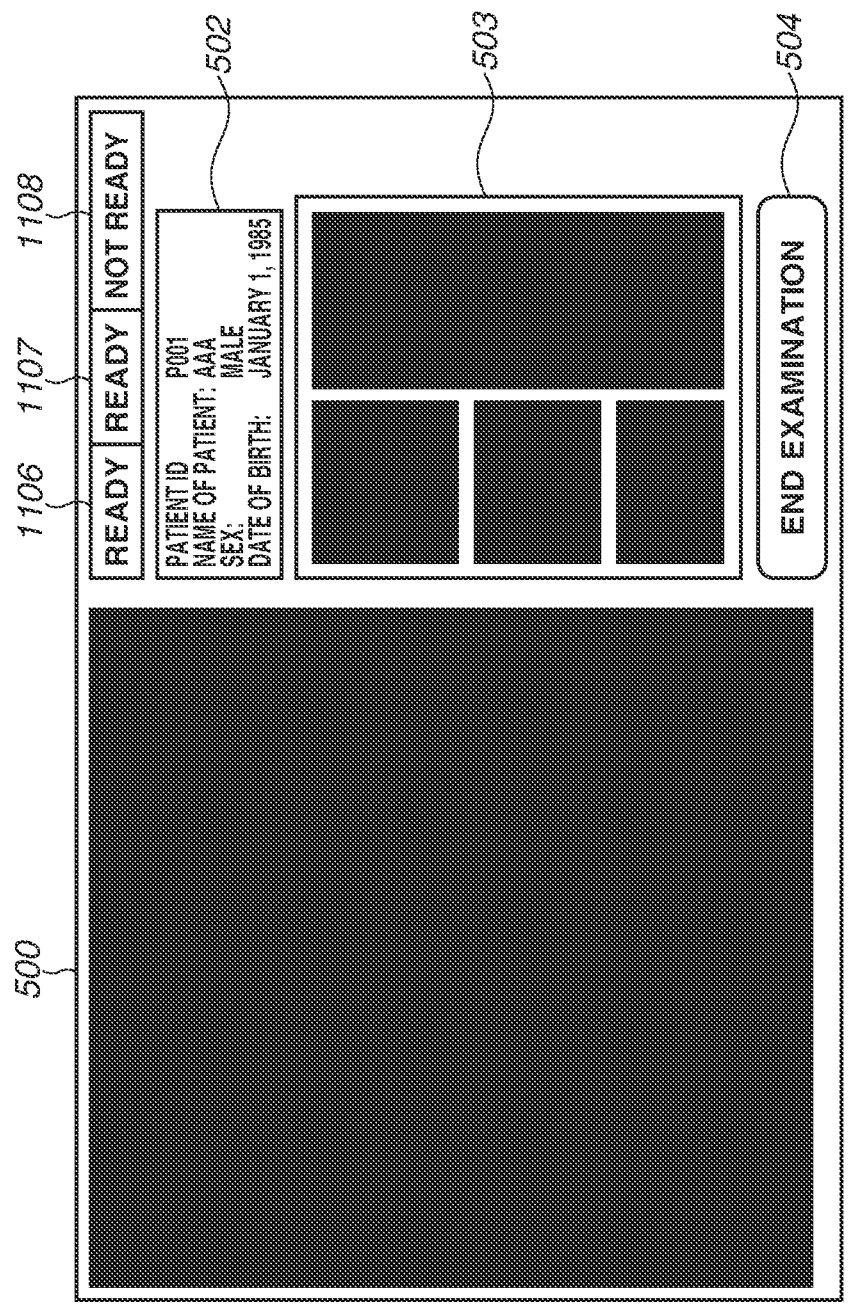

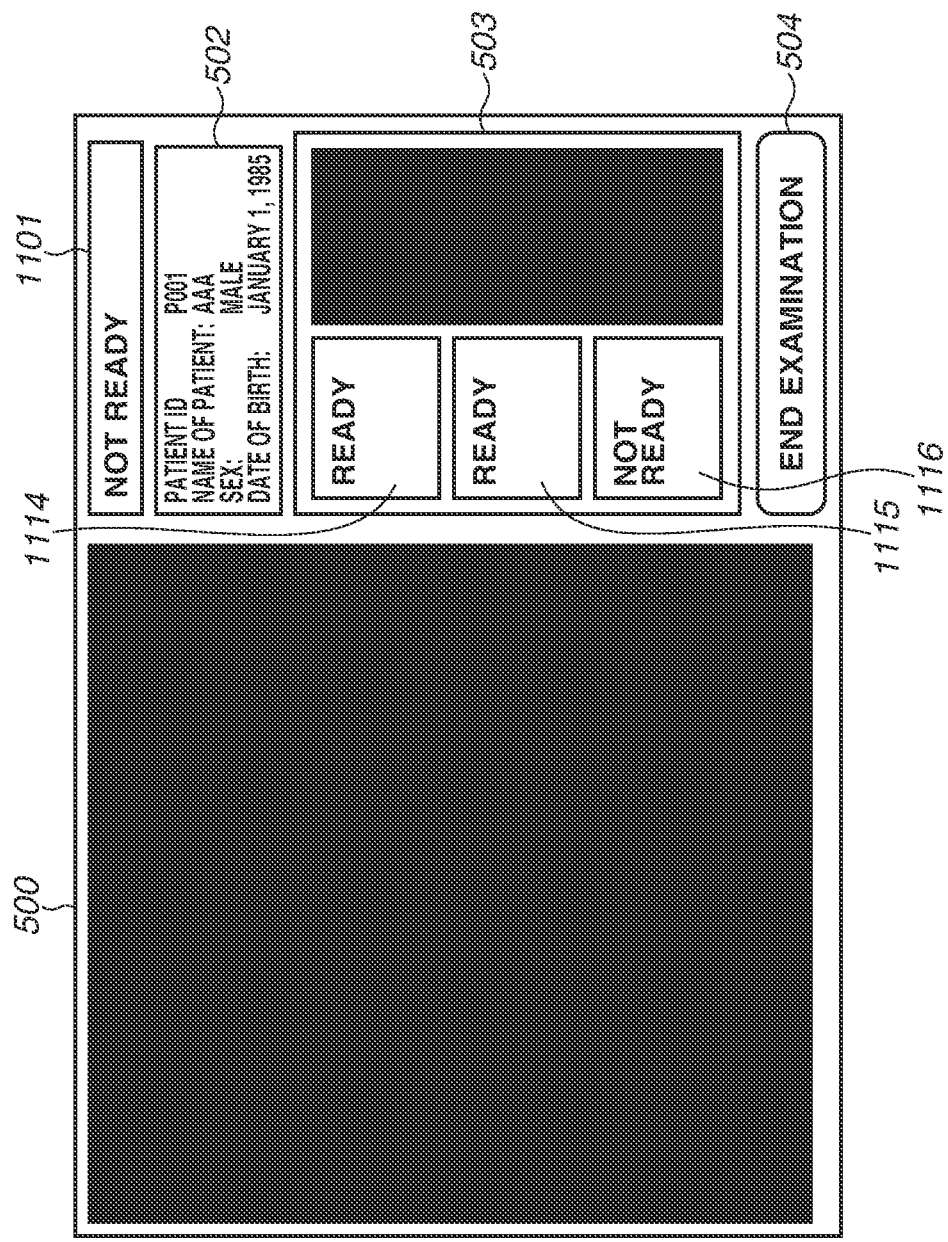

CONTROL APPARATUS, CONTROL METHOD, AND STORAGE MEDIUM

CROSS-REFERENCE TO RELATED APPLICATIONS

This application is a Continuation of U.S. patent application Ser. No. 16/122,686, filed Sep. 5, 2018, which is a continuation of U.S. patent application Ser. No. 15/008,988, filed Jan. 28, 2016, now U.S. Pat. No. 10,104,311 B2, issued Oct. 16, 2018, which claims foreign priority benefit of Japanese Patent Application No. 2015-017888, filed Jan. 30, 2015. All of the above-named applications are hereby incorporated by reference herein in their entirety.

BACKGROUND OF THE INVENTION

Field of Invention

The present invention relates to a radiographing system using a plurality of radiographic imaging units.

Description of the Related Art

As one of image-capturing methods using a radiographic imaging unit, such as a film cassette, an imaging plate based on the Computed Radiography (CR) method, or a digital radiation detector, there is stitch imaging for capturing a larger subject than a region where a single radiographic imaging unit detects radiation.

Methods for implementing the stitch imaging include a method that lays out a plurality of radiographic imaging units and irradiates the subject with a single shot of radiation, besides a method that irradiates the subject with a plurality of shots of radiation while moving a single radiographic imaging unit. A plurality of radiographic images acquired by any of these methods is appropriately arranged and stitched, by which an image of the larger subject than the region where the single radiographic imaging unit detects radiation can be acquired.

A stitch imaging system using the plurality of radiographic imaging units requires all of the plurality of radiographic imaging units to be prepared for the detection of the radiation before the subject is irradiated with the radiation.

SUMMARY OF THE INVENTION

According to an aspect of the present invention, a control apparatus for stitch imaging using a plurality of radiographic imaging units, includes a communication circuit configured to receive state information indicating whether each of the plurality of radiographic imaging units is in a first state, which is not a state prepared for acquisition of a radiographic image, or a second state, which is the state prepared for the acquisition of the radiographic image, from each of the plurality of radiographic imaging units, a determination unit configured to make a first determination, which determines that any one of the plurality of radiographic imaging units is in the first state, or a second determination, which determines that all of the plurality of radiographic imaging units are in the second state, based on the state information received from each of the plurality of radiographic imaging units, and a display control unit configured to control a display of a display unit according to whether the determination made by the determination unit is the first determination or the second determination.

Further features of the present invention will become apparent from the following description of exemplary embodiments with reference to the attached drawings.

BRIEF DESCRIPTION OF THE DRAWINGS

FIGS. 11A, 11B, 11C, and 11D illustrate examples of the display screen. In particular, FIG. 11A illustrates an example of the display screen according to the exemplary embodiment, FIG. 11B illustrates an example of the display screen according to the other exemplary embodiment, FIG. 11C illustrates information displayed according to an operation input entered on the display screen, and FIG. 11D illustrates an example of the display screen according to the other exemplary embodiment.

DESCRIPTION OF THE EMBODIMENTS

Figure 1:
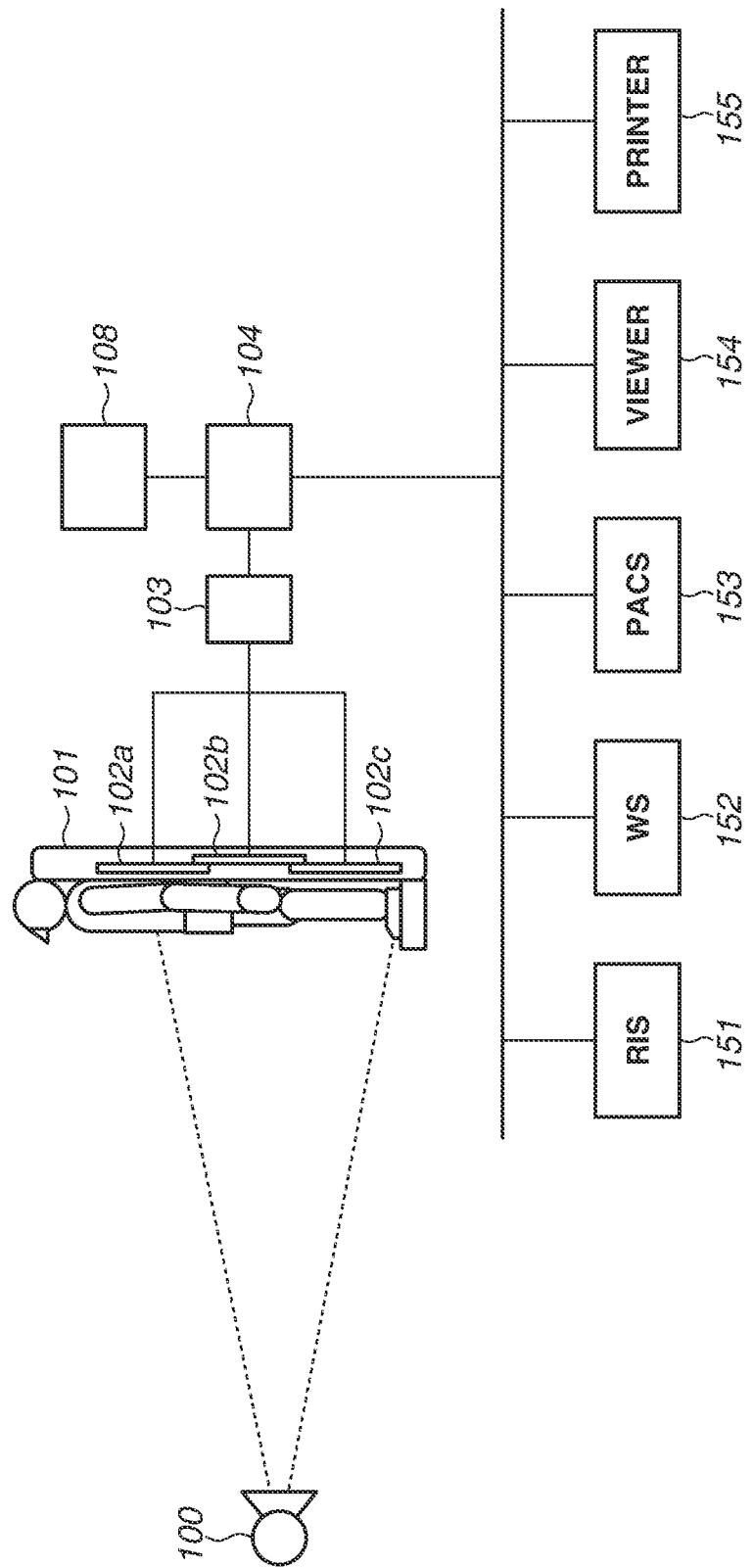
FIG. 1 is a block diagram illustrating a configuration of an information system including a radiographing system according to an exemplary embodiment.

A radiographing system according to an exemplary embodiment will be described with reference to FIG. 1. FIG. 1 illustrates a configuration of an information system including a stitch imaging system using an X-ray as radiation, which is an example of the radiographing system. This information system includes, for example, the radiographing system, a radiology information system (RIS) 151, a workstation (WS) 152, a picture archiving and communication system (PACS) 153, a viewer 154, and a printer 155. The RIS 151 is a system that manages an order for radiographic imaging, and transmits the order for radiographic imaging to the radiographing system. The WS 152 is an image processing terminal, and processes a radiographic image captured by the radiographing system to acquire an image for use in diagnosis. The PACS 153 is a database system that contains medical images provided from the radiographing system and another modality (a medical imaging system or a medial image-capturing apparatus). The PACS 153 includes a storage unit that stores the medical images and appendant information, such as image-capturing conditions applied for these medical images, and a controller that manages the information stored in this storage unit. The viewer 154 is a terminal for use in image diagnosis, and reads out the image stored in the PACS 153 or the like to display this image for the diagnosis. The printer 155 is, for example, a film printer, and outputs the image stored in the PACS 153 onto a film.

The stitch imaging system, which is an example of the radiographing system, includes a radiation generation unit 100, a platform 101, a plurality of radiographic imaging units 102a, 102b, and 102c (or a cassette A, a cassette B, and a cassette C), a relay 103, a control apparatus 104, and a touch panel monitor 108 that serves as both a display unit and an operation unit. These components are connected to one another via a cable. The radiation generation unit 100 emits the radiation to the plurality of radiographic imaging units 102a, 102b, and 102c simultaneously for irradiation. When the radiation is emitted to the plurality of radiographic imaging units 102a, 102b, and 102c for the irradiation, the plurality of radiographic imaging units 102a, 102b, and 102c acquires radiographic images, and this plurality of radiographic images is transmitted to the control apparatus 104 via the relay 103.

The control apparatus 104 is, for example, an electronic computer (a personal computer (PC)) with a desired software program installed therein, and generates a stitched image by performing image processing including stitching processing on this plurality of radiographic images. Further, the control apparatus 104 causes this stitched image to be displayed on the touch panel monitor 108. In this manner, the stitch imaging system carries out the stitch imaging of emitting the radiation to the plurality of radiographic imaging units 102a, 102b, and 102c simultaneously for the irradiation. Further, the control apparatus 104 generates a Digital Imaging and Communications in Medicine (DICOM) image based on this stitched image and appendant information, such as an image-capturing condition applied for this stitched image. Then, the control apparatus 104 transmits this DICOM image to the WS 152 or the PACS 153.

An image-capturing order for the stitch imaging is, for example, transmitted from the RIS 151 to the control apparatus 104. In this case, the control apparatus 104 receives, from the RIS 151, an image-capturing information identification (ID) indicating the stitch imaging, and information indicating an image-capturing site that should be captured by the stitch imaging, such as an entire lower limb and an entire spine, and reads out an image-capturing condition corresponding to this received information from a storage unit of the control apparatus 104. Alternatively, the control apparatus 104 may be assumed to acquire image-capturing information including information indicating the image-capturing site, an image-capturing method, and the image-capturing condition from an operation input via the touch panel monitor 108.

Besides the touch panel monitor 108, an operation unit such as a mouse and a keyboard may be connected to the control apparatus 104.

As illustrated in FIG. 1, the radiographic imaging units 102a, 102b, and 102c are laid out in such a manner that a region that the radiographic imaging unit 102a captures and a region that the radiographic imaging unit 102b captures partially overlap each other so as to establish a continuous imaging region. This layout results in the appearance of a predetermined structure in the radiographic image acquired by the radiographic imaging unit 102b. On the platform 101 according to the present exemplary embodiment, only a radiographic imaging unit 102 disposed in the middle among the radiographic imaging units 102a, 102b, and 102c disposed in the order is located at a position farther away from the radiation generation unit 100 than the other radiographic imaging units 102, and is arranged in such a manner that the imaging region thereof partially overlaps the imaging regions of the other radiographic imaging units 102. Laying out the radiographic imaging units 102a, 102b, and 102c in this manner can reduce the number of radiographic images with the structure appearing therein.

The radiographic image with the structure appearing therein is corrected by, for example, the control apparatus 104 or the radiographic imaging unit 102 with use of correction data for correcting the structure that is separately acquired, so that the number of structures appearing in the radiographic image(s) is reduced.

Figure 2:
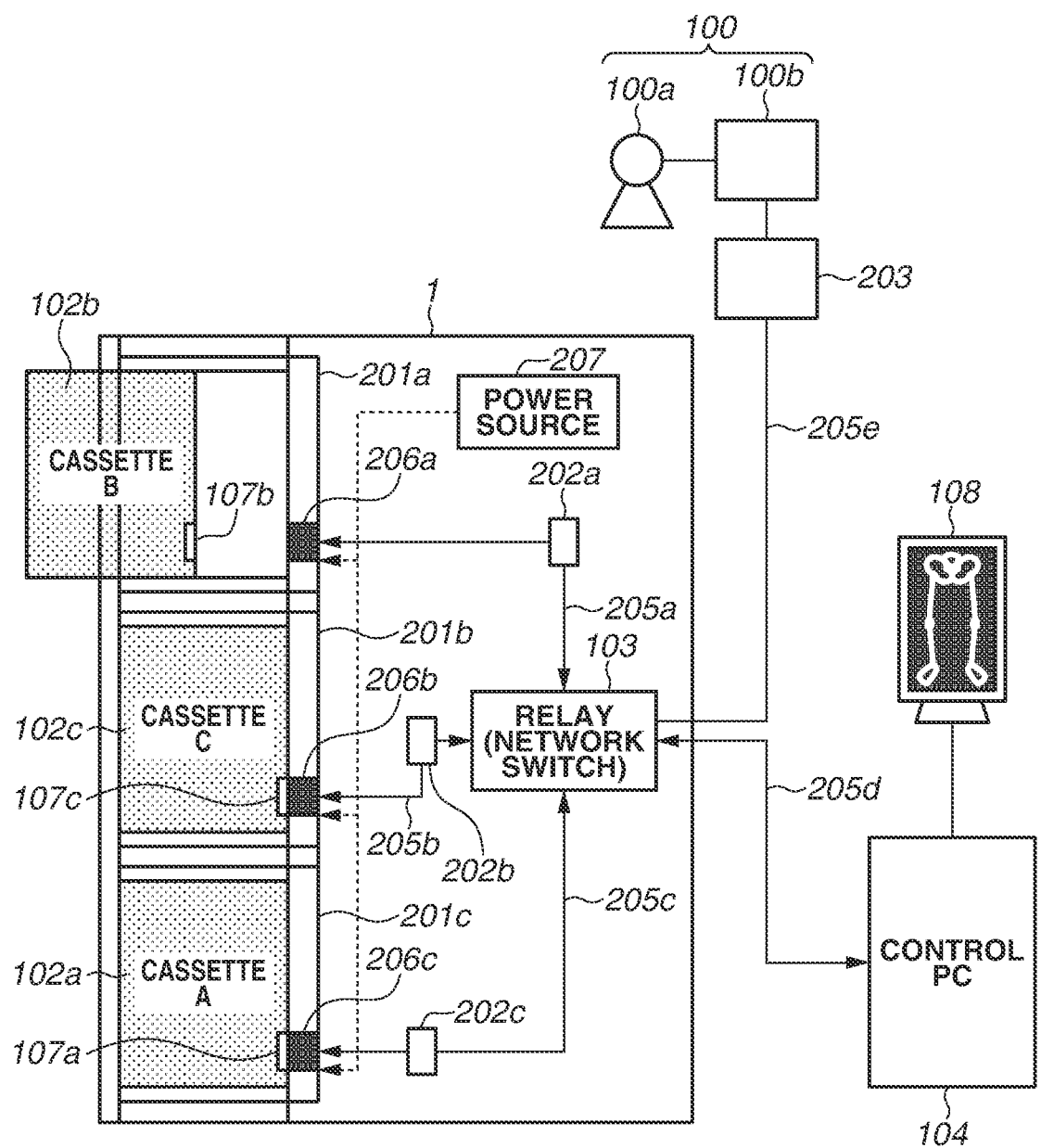
FIG. 2 is a block diagram illustrating a configuration of a stitch imaging system according to the exemplary embodiment.

A configuration of the stitch imaging system according to the present exemplary embodiment will be described in detail with reference to FIG. 2. The radiation generation unit 100 includes a radiation irradiation unit 100a that includes a diaphragm for setting a range to be irradiated with the radiation and a radiation source for generating the radiation, and a generation control unit 100b for controlling the irradiation with the radiation by the radiation irradiation unit 100a. An irradiation switch is further connected to the generation control unit 100b to input a signal for instructing the generation control unit 100b about a timing of starting the irradiation to the generation control unit 100b. The radiation generation unit 100 may further include an interface unit 203 that communicates with the radiographic imaging units 102a, 102b, and 102c. In this case, the radiation generation unit 100 and the platform 101 are connected communicably with each other via a network cable 205e, such as an Ethernet (registered trademark) cable. The control apparatus 104 is connected to the platform 101 communicably with each other via a network cable 205d.

The platform 101 is a holder unit that fixes the plurality of radiographic imaging units 102a, 102b, and 102c for carrying out the stitch imaging. In one exemplary embodiment, the platform 101 has three positions for fixing the radiographic imaging units 102a, 102b, and 102c, and includes a housing portion 201 that houses the radiographic imaging unit 102, and a platform connector 206 at each of the fixation positions. The position of each of the connectors 206 is determined in such a manner that the platform connector 206 and a radiographic imaging unit connector 107 are fitted to each other when the radiographic imaging unit 102 is fixed in the housing portion 201.

The platform 101 includes housing portions 201a, 201b, and 201c that house the radiographic imaging units 102a, 102b, and 102c, respectively, platform connectors 206a, 206b, and 206c respectively disposed along sidewalls of the housing portions 201a, 201b, and 201c and respectively provided for establishing wired connections with the radiographic imaging units 102a, 102b, and 102c, and the relay 103 (a network switch).

The platform connectors 206a, 206b, and 206c are connected to the relay 103 via network cables 205a, 205b, and 205c, respectively. Further, the platform connectors 206a, 206b, and 206c are connected to the radiographic imaging unit connectors 107 of the radiographic imaging units 102a, 102b, and 102c, respectively. In the example illustrated in FIG. 2, a radiographic imaging unit connector 107b of the radiographic imaging unit 102b, a radiographic imaging unit connector 107c of the radiographic imaging unit 102c, and a radiographic imaging unit connector 107a of the radiographic imaging unit 102a are connected to the platform connector 206a, the platform connector 206b, and the platform connector 206c, respectively.

The relay 103 is the network switch, and one of a plurality of physical ports thereof is extended out of the platform 101 so as to be connectable to the control apparatus 104. This port is fixedly wired so as to be connected to a communication port of the control apparatus 104, when the platform 101 and the control apparatus 104 are set up in a user's use environment. The remaining ports are wired so as to be connected to the platform connectors 206a, 206b, and 206c at the cassette fixation positions. This wiring is fixedly wired when the platform 101 is manufactured, so that corresponding relationships between the platform connectors 206a, 206b, and 206c and the physical ports of the relay 103 do not change over the course of the user's use.

The platform 101 may further include a power source 207 that supplies power to the radiographic imaging units 102a, 102b, and 102c. This configuration leads to connections of two cable systems, a network cable and a power source cable to each of the platform connectors 206a, 206b, and 206c. Instead of the power source 207, power source units 202a, 202b, and 202c may be provided with respect to the housing portions 201a, 201b, and 201c, respectively. This configuration leads to connections of two systems, a communication cable and a power source cable between the platform connector 206 and the power source unit 202, and a connection of a communication cable between the power source unit 202 and the relay 103.

The radiographic images provided from the radiographic imaging units 102a, 102b, and 102c are transmitted to the control apparatus 104 via the radiographic imaging unit connectors 107a, 107b, and 107c, the platform connectors 206a, 206b, and 206c, and the relay 103.

In another exemplary embodiment, the platform 101 may be configured to include a radiographic imaging unit connection unit and a platform connection unit that perform near field wireless communication, such as TransferJet, instead of the radiographic imaging unit connector 107 and the platform connector 206. Alternatively, the radiographic imaging unit 102 may be configured to wirelessly communicate with the relay 103 directly without communicating via the platform connector 206 and the like. This configuration leads to the radiographic imaging unit 102 wirelessly communicating with the platform 101 and the relay 103, and makes the communication path partially wireless between the radiographic imaging unit 102 and the control apparatus 104.

The relay 103 is disposed inside the platform 101, but is not limited thereto and may be disposed outside the platform 101. Further, the relay 103 and the radiation generation unit 100 may be connected to each other via a wireless communication path, and the relay 103 and the control apparatus 104 may be connected to each other via a wireless communication path.

To carry out the stitch imaging, first, the radiographic imaging units 102a, 102b, and 102c are fixedly mounted onto the respective fixation positions of the platform 101 provided for the stitch imaging. By this mounting, the platform connectors 206a, 206b, and 206c and the radiographic imaging unit connectors 107a, 107b, and 107c are fitted to each other, respectively. By this fitting, respective main control circuits inside the individual radiographic imaging units 102a, 102b, and 102c are connected to the relay 103 via the radiographic imaging unit connectors 107a, 107b, and 107c, the platform connectors 206a, 206b, and 206c, and the network cables 205a, 205b, and 205c, respectively. As a result, a network including the individual radiographic imaging units 102a, 102b, and 102c and the control apparatus 104 is created. The radiographic imaging units 102a, 102b, and 102c and the relay 103 are connected in an individually attachable and detachable manner by the fitted attachment between the radiographic imaging unit connectors 107a, 107b, and 107c and the platform connectors 206a, 206b, and 206c.

The creation of the network allows each of the cassettes A, B, and C and the control apparatus 104 to communicate with each other, thereby causing the software of the control apparatus 104 to start control communication with each of the cassettes A, B, and C. This control communication allows the software of the control apparatus 104 to recognize that each of the radiographic imaging units 102a, 102b, and 102c is mounted on the platform 101, and also recognize a position where each of the cassettes A, B, and C is mounted on the holder. How the position recognition proceeds will be described below.

When the user completes the operation of mounting the radiographic imaging units 102a, 102b, and 102c, and the software can confirm that the radiographic imaging units 102a, 102b, and 102c are mounted normally, the software displays the completion of the preparation on the touch panel monitor 108 connected to the control apparatus 104. The user confirms the display indicating the completion of the preparation, and carries out the image-capturing. As illustrated in FIG. 1, the image-capturing is carried out in such a manner that a subject is positioned in front of the platform 101, and the subject in a wide range extending across the plurality of radiographic imaging units 102a, 102b, and 102c can be imaged by being irradiated with the radiation a single time.

After the image-capturing is carried out, a main control circuit 150 of each of the cassettes A, B, and C generates image data by scanning a two-dimensional image sensor 120. The generated image data is transferred to the control apparatus 104. In this case, the image data may be transferred with use of a communication path via a wired communication circuit 180 and the radiographic imaging unit connector 107 built in the radiographic imaging unit 102, the platform connector 206, and the like. Alternatively, the image data may be transferred via a wireless communication circuit 160 built in the radiographic imaging unit 102, and a not-illustrated wireless access point connected to the control apparatus 104.

The control apparatus 104 performs image processing for rearranging the images received from the individual radiographic imaging units 102a, 102b, and 102c by referring to recognized information about the positions where the cassettes A, B, and C are mounted, and connectively combines them. The combined image is presented to the user as a stitch imaging image that contains information of the subject in the wide range.

Figure 3:
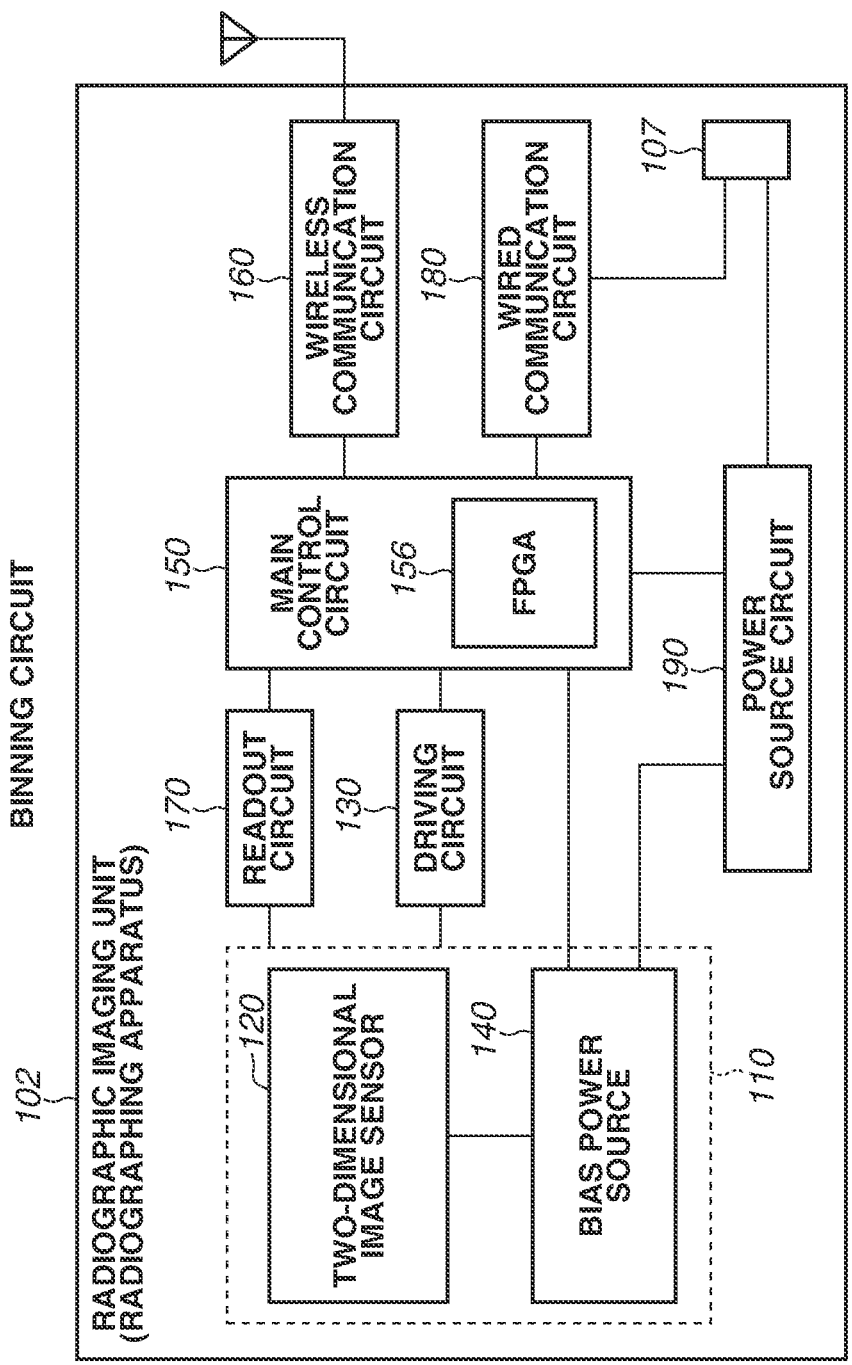
FIG. 3 is a block diagram illustrating a configuration of a radiographic imaging unit according to the exemplary embodiment.

A configuration of the radiographic imaging unit (a radiographing apparatus) 102 according to the present exemplary embodiment will be described with reference to FIG. 3. The radiographic imaging unit 102 includes a radiation sensor 110, a driving circuit 130, a readout circuit 170, the main control circuit 150, the wireless communication circuit 160, the wired communication circuit 180, the radiographic imaging unit connector 107, and a power source circuit 190. The radiation sensor 110 includes the two-dimensional image sensor 120. The two-dimensional image sensor 120 includes a pixel array in which a plurality of pixels is arrayed in the form of a matrix, a row selection line that is commonly connected to pixels lined up in a row direction and transmits a driving signal issued from the driving circuit 130, and a column signal line that is commonly connected to pixels lined up in a column direction and transmits an image signal to the readout circuit 170. A bias power source 140 is connected to each of the pixels of the two-dimensional image sensor 120. The pixels each include a photoelectric conversion element having one end connected to the bias power source 140, and a switching element connected to another end of this photoelectric conversion element. A base electrode of the switching element is connected to the row selection line, and the photoelectric conversion element and the column signal line are connected to a collector and an emitter of the switching element. The two-dimensional image sensor 120 generates the image based on a distribution of intensity of the radiation incident on this image sensor 120.

Other than those, the radiation sensor 110 may include a binning circuit that includes a switching element for connecting a plurality of pixels to one another, and combines image signals. For example, the switching element is connected to four pixels, vertically adjacent two pixels and horizontally adjacent two pixels. This configuration allows the radiation sensor 110 to combine the image signals before the image signals are digitized.

The driving circuit 130 controls an on state and an off state of the switching element by outputting the driving signal. When the switching element is controlled into the off state, this causes the image signal to be stored into a parasitic capacitance or the like of the photoelectric conversion element. When the switching element is controlled into the on state, this causes the stored image signal to be output via the column signal line. The readout circuit 170 includes an amplifier for amplifying the image signal output from the radiation sensor 110, and an analog-to-digital (A/D) converter for converting the image signal into a digital signal. The image signal is read out as the digital signal by them.

The driving circuit 130 performs control of collectively applying off-state voltages and control of sequentially applying on-state voltages to the row selection lines corresponding to the individual rows of the pixel array. The off-state voltages cause the radiation sensor 110 to transition to a storage state. The control of sequentially applying the on-state voltages causes the signals of the pixel array to be sequentially output to the readout circuit 170. By theses control procedures, the radiographic imaging unit 102 performs an operation of initializing the pixel array before causing the radiation sensor 110 to transition to the storage state, and an operation of reading out the image signals acquired from the storage.

The driving circuit 130 may conduct interlace driving of sequentially applying the on-state voltages to 2n rows, i.e., even-numbered rows, and then sequentially applying the on-state voltages to 2n−1 rows, i.e., odd-numbered rows after that. By this driving, the driving circuit 130 realizes reading out the image signals while thinning out the image signals. The thinning-out driving is not limited to the method that conducts this driving at intervals of one row as described above, and may be set to be conducted at intervals of two rows or m−1 rows. A desired value is adopted as a rate at which the image signals are thinned out in this manner. The driving circuit 130 may be set to sequentially apply the on-state voltages, like sequentially applying the on-state voltages to an mn row, an mn+1 row, an mn+2 row, . . . and an mn+(m−1) row, when m−1 is set as the rate at which the image signals are thinned out.

Alternatively, the driving circuit 130 can also conduct partial readout of the image signals, which means outputting image signals acquired from pixels around a center of the pixel array prior to the other image signals. In this case, supposing that the pixel array is constituted by M rows and N columns, M/2×N/2 image signals of an M/4+1 row to a 3M/4 row and an N/4+1 column to a 3N/4 column are output. The above-described operations performed by the driving circuit 130 are performed according to control from the main control circuit 150.

The main control circuit 150 integrally controls the radiographic imaging unit 102. Further, the main control circuit 150 includes a processing circuit implemented by a field-programmable gate array (FPGA) 156, and generates the radiographic image and performs the image processing thereby. The FPGA 156 can perform processing for acquiring an image small in data amount by, for example, the binning processing that sums up values of the adjacent 2×2 pixels, the thinning-out processing that partially thins out the pixels and partially extracts the pixels, or processing that extracts a continuous region, when acquiring the digital radiographic image.

Further, examples of the image processing that may be performed by the FPGA 156 include a dark correction for reducing a dark current component in the radiographic image, a gain correction for correcting a variation in an input/output characteristic of the pixel, a correction of a defective pixel, and processing for reducing a noise, such as a line noise.

The wireless communication circuit 160 and the wired communication circuit 180 can transmit and receive a control command and data, such as a signal from the control apparatus 104 and the radiation generation unit 100. Further, the wireless communication circuit 160 transmits a signal indicating a state of the radiographic imaging unit 102, and the radiographic image. The wireless communication circuit 160 includes an antenna, and performs wireless communication mainly when the wired cable 205 is not connected to the radiographic imaging unit connector 107. The radiographic imaging unit connector 107 is connected to the wired communication circuit 180, and the wired communication circuit 180 controls the wired communication. The connector 107 is provided for the communication and the power supply, and the communicated information and the power are transmitted to the wired communication circuit 180 and the power source circuit 190, respectively. The power source circuit 190 includes a battery, and produces a voltage required for the operation of the radiographic imaging unit 102 to supply the voltage to each of the units. The main control circuit 150 specifies which communication method should be used, the wireless communication or the wired communication. For example, the wired communication is specified if the wired cable 205 is connected to the connector 107, and the wireless communication is specified if the wired cable 205 is not connected but a connection via the wireless communication is established. Neither communication method is specified if the wired cable 205 is not connected and a connection via the wireless connection is also not established. In this case, for example, the radiographic image is not transmitted, and is stored into a nonvolatile memory connected to the main control circuit 150.

If transmitting the radiographic image with any of the communication methods specified, the main control circuit 150 transfers a preview image smaller in data amount than the radiographic image acquired by the radiation sensor 110 prior to this radiographic image. Then, the main control circuit 150 transmits an image that contains data uncontained in the preview image after completion of the transmission of this preview image.

This transmission allows the control apparatus 104 side to quickly check whether the image-capturing has been appropriate. The preview image and the image that contains the data uncontained in the preview image may be transmitted according to the readout of the image signals by the readout circuit 170 and the generation of the preview image by the main control circuit 150. Alternatively, the main control circuit 150 may be set to transmit these images according to a signal from the control apparatus 104. In this manner, the control apparatus 104 controls the communication with the plurality of radiographic imaging units 102a, 102b, and 102c, which can reduce an influence due to simultaneous transmission of large-volume data from the plurality of radiographic imaging units 102a, 102b, and 102c, thereby realizing efficient image communication.

Because this influence on the communication can be less likely to arise in some cases, for example, when the radiographic imaging unit 102 is connected to the control apparatus 104 via the wired communication or the communication capacity is sufficiently large, the main control circuit 150 may be configured to change the method for transmitting the images according to the communication method between the control apparatus 104 and the radiographic imaging unit 102.

One of states of the radiographic imaging unit 102 is a first state in which power is supplied only to the wireless communication circuit 160 and the wired communication circuit 180, and no power is supplied from the bias power source 140 to the two-dimensional image sensor 120 (a so-called sleep state). Further, another state of the radiographic imaging unit 102 is a second state in which power is supplied from the bias power source 140 to the two-dimensional image sensor 120. In the second state, the initialization operation is conclusively performed, and the radiographic imaging unit 102 is ready to generate the image by transitioning to the storage state in response to an instruction from outside. The radiographic imaging unit 102 transmits the signal indicating the above-described state according to a request signal from outside.

In a case where the radiation generation unit 100 is provided with the interface unit 203, synchronized communication is performed between the radiation generation unit 100 and the radiographic imaging unit 102. In response to pressing of the irradiation switch, the interface unit 203 transmits a first signal to each of the radiographic imaging units 102a, 102b, and 102c. According to this first signal, the driving circuit 130 of each of the radiographic imaging units 102a, 102b, and 102c causes the two-dimensional image sensor 120 to perform the initialization operation, and to transition to the storage state. Upon completion of the initialization and the transition to the storage state, each of the radiographic imaging units 102a, 102b, and 102c transmits a second signal to the interface unit 203. The interface unit 203 determines whether the second signals are received from all of radiographic imaging units 102 to be used for a certain stitch imaging, and inputs a signal for permitting the irradiation to the generation control unit 100b if the interface unit 203 has determined that the second signals are received from all of them. According thereto, the radiation is emitted from the radiation irradiation unit 100a for the irradiation. Controlling the units in this manner can prevent the radiation irradiation from being carried out before the radiographic imaging units 102a, 102b, and 102c transition to the storage state, thereby reducing unnecessary exposure.

In a case where the radiation generation unit 100 is not provided with the interface unit 203, the radiation generation unit 100 irradiates the subject with the radiation in response to the pressing of the irradiation switch. Each of the radiographic imaging units 102a, 102b, and 102c detects this start of the radiation irradiation, and transitions to the storage state. The radiographic imaging unit 102a, 102b, and 102c may each detect the start of the irradiation based on a signal acquired by the two-dimensional image sensor 120, or may detect the start of the irradiation by a sensor for detecting the start of the irradiation that is provided separately from the radiation sensor 110.

The main control circuit 150 specifies which mode should be employed, a first image-capturing mode of performing the synchronized communication or a second image-capturing mode of detecting the radiation, according to a signal input from outside.

Figure 4:
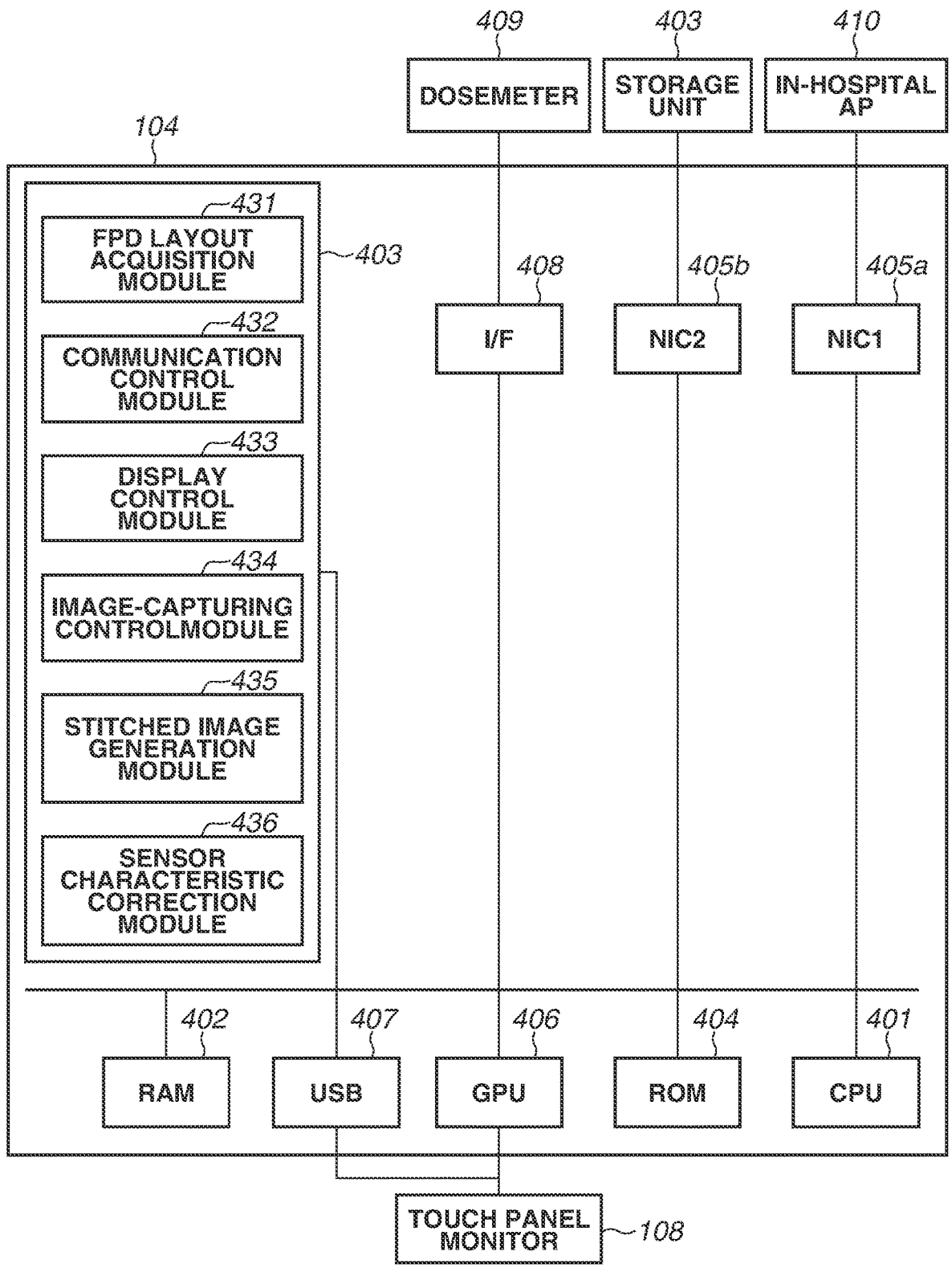
FIG. 4 is a block diagram illustrating a configuration of a control apparatus according to the exemplary embodiment.

A configuration of the control apparatus 104 according to the present exemplary embodiment will be described with reference to FIG. 4. The control apparatus 104 includes a central processing unit (CPU) 401, a random access memory (RAM) 402, a storage unit 403, a read only memory (ROM) 404, network interface cards (NICs) 405 (405a and 405b), a graphic processing unit (GPU) 406, a universal serial bus (USB) interface 407, and a communication interface (I/F) 408. These components are communicably connected to one another via an internal bus. The CPU 401 is a control circuit that comprehensively controls the control apparatus 104 and each of units connected to the control apparatus 104, and may include a plurality of CPUs. The RAM 402 is a memory used for loading a program for performing, for example, processing illustrated in FIG. 6 that will be described below, and various kinds of parameters, which are stored in the storage unit 403 or the like. The CPU 401 sequentially executes commands contained in the program loaded into this RAM 402, by which the processing according to the present exemplary embodiment is realized. The storage unit 403 is a memory such as a hard disk drive (HDD) and a solid state drive (SSD), and stores the above-described program, the radiographic image such as the stitched image acquired by the image-capturing, the image-capturing order, the image-capturing information, and in addition thereto, the various kinds of parameters. The NICs 405 are an example of a communication unit that communicates with an external apparatus. The control apparatus 104 according to the present exemplary embodiment includes a first NIC 405a and a second NIC 405b. The first NIC 405a is connected to an in-hospital access point (AP) 410 for connecting to an in-hospital network, and the second NIC 405b is connected to the relay 103 that relays the communication of the radiographing system. The GPU 406 is an image processing unit, and performs the image processing according to control from the CPU 401. An image acquired as a result of the image processing is output and displayed onto the touch panel monitor 108. The USB I/F 407 is a communication unit that acquires information relating to an operation input from the touch panel monitor 108, and is interpreted as the operation input by the CPU 401. The communication I/F 408 is, for example, a communication unit supporting a standard such as Recommended Standard 232 version C (RS232C), Ethernet (registered trademark), and USB, and communicates with a dosemeter (a dose measurement device) 409 to receive information indicating a radiation dose.

The program stored in the storage unit 403 includes, for example, a flat panel detector (FPD) (radiographic imaging unit) layout acquisition module 431, a communication control module 432, a display control module 433, an image-capturing control module 434, a stitched image generation module 435, and a correction module 436.

The FPD layout acquisition module 431 acquires information indicating a layout relationship among the plurality of radiographic imaging units 102a, 102b, and 102c to be used to carry out the one stitch imaging. The information indicating the layout relationship is, for example, information indicating that the radiographic imaging units 102a, 102b, and 102c are laid out so as to be arranged in this order, or information indicating that the radiographic imaging unit 102b is located in the middle of them. The information indicating the layout relationship may contain information indicating rotational states of the radiographic imaging units 102a, 102b, and 102c. Such information indicating the layout relationship is acquired by the CPU 401 based on, for example, information, received by the second NIC 405b, indicating the communication paths of the radiographic imaging units 102a, 102b, and 102c, and correspondence information, stored in the storage unit 403, indicating correspondence relationships between the communication paths and the layout positions. For example, in a case where the platform connectors 206a, 206b, and 206c are disposed fixedly relative to the housing portions 201a, 201b, and 201c as illustrated in FIG. 2, the layout positions of the plurality of radiographic imaging units 102a, 102b, and 102c can be identified by referring to the information indicating the communication paths. For example, in a case where the relay 103 is a layer 2 network switch, the relay 103 performs an operation of learning relationships between the physical ports and media access control (MAC) addresses, and correspondence relationships between the radiographic imaging units 102a, 102b, and 102c and the physical ports are acquired as the information indicating the communication paths with use of this operation.

This information indicating the layout relationships acquired in this manner is stored into the storage unit 403. Alternatively, the second NIC 405b may receive the information indicating the layout relationship. In this case, the relay 103 or the platform 101 is assumed to have a function of acquiring the information indicating the layout relationship based on the information indicating the communication paths and the like.

The information indicating the layout relationship is, for example, referred to during the course of execution of the stitched image generation module 435, and used in the processing for stitching the plurality of radiographic images. The information indicating the layout relationship in this case is information for identifying which radiographic images contain an overlap region therebetween. Further, the information indicating the layout relationship is, for example, referred to by the CPU 401 to determine which radiographic image should be subjected to execution of the correction processing for removing the structure appearing therein during the course of execution of the correction module 436. The information indicating the layout relationship in this case is information for identifying which one of the radiographic imaging units 102a, 102b, and 102c has output the image with the structure appearing therein, and corresponds to information for identifying which one of the radiographic imaging units 102a, 102b, and 102c radiographic imaging unit is located in the middle of the radiographic imaging units 102a, 102b, and 102c in the imaging system illustrated in FIG. 1.

The communication control module 432 controls the communication by the first NIC 405a and the second NIC 405b. Execution of the communication control module 432 causes, for example, the control apparatus 104 to transmit the signals for causing the states of the plurality of radiographic imaging units 102a, 102b, and 102c to transition to the second state to the radiographic imaging units 102a, 102b, and 102c according to an operation input from the touch panel monitor 108 or the like. This operation input is carried out, for example, according to an operation input for selecting one of a plurality of image-capturing conditions contained in the image-capturing order and then the CPU 401 specifying this image-capturing condition based thereon. In response to this operation input, the second NIC 405b transmits the signals for causing the states to transition, to the radiographic imaging units 102a, 102b, and 102c. Then, the second NIC 405b will receive response signals thereto.

Further, the execution of the communication control module 432 causes, for example, the control apparatus 104 to receive the radiographic image from each of the plurality of radiographic imaging units 102a, 102b, and 102c. At this time, the control apparatus 104 is assumed to first receive the preview image (a first image) small in data amount and then receive the image that contains the remaining data (a second image) after that, from each of the plurality of radiographic imaging units 102a, 102b, and 102c. In this case, the control apparatus 104 is assumed to, when receiving the preview image (the first image) from one radiographic imaging unit 102, restrict the reception of the first or second image from the other radiographic imaging units 102. Therefore, each of the radiographic imaging units 102a, 102b, and 102c is assumed to be set to transmit the image according to an instruction from the control apparatus 104, and the control apparatus 104 is assumed to instruct one radiographic imaging unit 102 to transmit the second image according to, for example, completion of the reception of the preview images (the first images) from all of the radiographic imaging units 102a, 102b, and 102c. By this control, the large-volume data is prevented from being transmitted from the plurality of radiographic imaging units 102a, 102b, and 102c to the relay 103 simultaneously, thereby improving efficiency of the communication.

The radiographic imaging unit side can also perform a transmission method in which the radiographic image is transmitted in response to the readout of the image signals (a first transmission method), besides the transmission method in which the image is transmitted in response to the instruction signal as described above (a second transmission method). The transmission method to be performed is, for example, specified according to a signal from the control apparatus 104. For example, the first transmission method is specified in the case where the radiographic imaging unit 102 performs the wired communication, and the second transmission method is specified in the case where the radiographic imaging unit 102 performs the wireless communication. In the case where the transmission method is specified according to the communication configuration in this manner, the radiographic imaging unit 102 can specify the transmission method regardless of the signal from outside.

Besides that, by executing the communication control module 432, the CPU 401 cause a DICOM image file containing the radiographic image acquired by the radiographic imaging or the stitch imaging to be transmitted to the PACS 153 via the first NIC 405a.

In one exemplary embodiment, the FPGA 156 of the radiographic imaging unit 102 performs the processing for correcting the structure appearing in the radiographic image. In this case, the CPU 401 specifies the radiographic imaging unit 102 to be instructed to perform the processing for correcting the structure among the plurality of radiographic imaging units 102a, 102b, and 102c during the course of the execution of the communication control module 432. As an example thereof, the radiographic imaging unit 102b located in the middle of the radiographic imaging units 102a, 102b, and 102c illustrated in FIG. 1 is specified with use of the information indicating the layout relationship. Then, the CPU 401 causes the second NIC 405b to transmit an instruction signal for instructing the radiographic imaging unit 102b to perform the processing for correcting the structure to the radiographic imaging unit 102b.

The display control module 433 is used in processing for controlling a content of a display screen displayed on the touch panel monitor 108. This processing is, for example, processing for displaying the image-capturing condition corresponding to the stitch imaging and processing for displaying the generated stitched image on the display screen. Further, by this module, the CPU 401 determines whether any one of the above-described plurality of radiographic imaging units 102a, 102b, and 102c is in the first state or all of the above-described plurality of radiographic imaging units 102a, 102b, and 102c are in the second state based on the information indicating the respective states of the plurality of radiographic imaging units 102a, 102b, and 102c. Then, the CPU 401 controls the display of the touch panel monitor 108 according to this determination. The second NIC 405b receives the state information indicating whether the radiographic imaging unit 102 is in the first state, which is not a state prepared for the acquisition of the radiographic image, or the second state, which is the state prepared for the acquisition of the radiographic image, with respect to each of the plurality of radiographic imaging units 102a, 102b, and 102c. The CPU 401 determines whether any one of the above-described plurality of radiographic imaging units 102a, 102b, and 102c is in the first state or all of the above-described plurality of radiographic imaging units 102a, 102b, and 102c are in the second state.

Controlling the display in this manner allows the control apparatus 140 to present a display indicating whether all of the radiographic imaging units 102a, 102b, and 102c are in the state capable of the image-capturing, instead of a display individually indicating the state of each of the radiographic imaging units 102a, 102b, and 102c, thereby allowing the user to intuitively recognize whether the stitch imaging can be carried out. Alternatively, the control apparatus 104 may also be configured to present the display individually indicating the state of each of the radiographic imaging units 102a, 102b, and 102c, together with the display indicating whether all of the radiographic imaging units 102a, 102b, and 102c are in the state capable of the image-capturing, and it is apparent that such a display allows the user to readily take some measures, for example, when one radiographic imaging unit 102 cannot carry out the image-capturing due to an error.

The image-capturing control module 434 is a program for causing the CPU 401 to integrally control the execution of the radiographic imaging including the stitch imaging. By the image-capturing control module 434, for example, the CPU 401 specifies the image-capturing condition according to the operation input, transmits the signal for requesting the state of each of the units of the radiographic imaging unit 102, and controls the reception of the radiographic images.

The stitched image generation module 435 generates the stitched image from the plurality of radiographic images with use of the CPU 401 and the GPU 406. The stitched image is generated by positioning processing for defining a positional relationship among the plurality of radiographic images. The positioning processing includes rough adjustment processing for determining a rough layout among the images, and fine adjustment processing for adjusting the positions among the images with precision of several pixels, or precision of one pixel or less.

The rough adjustment processing is processing for determining which ends correspond to each other among the ends of the individual radiographic images with use of the information indicating the layout relationship among the plurality of radiographic imaging units 102a, 102b, and 102c. This processing is performed with use of the layout information acquired from the processing performed by the FPD layout acquisition module 431. The fine adjustment processing is performed by, for example, pattern matching processing with use of image information of a region overlapping among the plurality of radiographic images. This processing may be performed after the processing by the correction module 436.

The correction module 436 performs the processing for correcting an influence due to the characteristic of the sensor and the correction processing for reducing the number of structures appearing in the radiographic image(s) with use of the CPU 401 and the GPU 406. The processing for correcting the characteristic of the sensor includes, for example, the processing for correcting influences of the variation in the input/output characteristic of each of the pixels, the defective pixel, and the like, and this processing is performed with use of data such as data for the gain correction and a defective map that are acquired in advance. The correction processing for reducing the number of structures appearing in the radiographic image(s) is performed with use of the correction data for reducing the number of structures. This correction data is acquired by subtracting data acquired by carrying out the image-capturing with use of the same imaging system as the imaging system that captures this radiographic image and without the presence of the subject, after dividing this data by the data for the gain correction or dividing this data thereby after logarithmically converting this data. This correction data may be stored in the radiographic imaging unit 102 in advance at the time of shipment from a factory or the like, or may be acquired before the stitch imaging is carried out in each hospital.

In another exemplary embodiment, the function of the relay 103 is assumed to be provided to the control apparatus 104. In this case, the stitch imaging system is configured in such a manner that, for example, the control apparatus 104 includes three second NICs 405b that communicate with the radiographic imaging units 102a, 102b, and 102c, and cables connected to the radiographic imaging units 102a, 102b, and 102c are directly connected to the control apparatus 104.

The display screen according to the present exemplary embodiment will be described with reference to FIG. 5. A display screen 500 includes an image area 501 where the radiographic image is displayed, a subject area 502 where information about the subject is displayed, a image-capturing information area 503 where the image-capturing information is displayed, an end button 504, and a state area 507 where information indicating the states of the plurality of radiographic imaging units 102a, 102b, and 102c is displayed. The example illustrated in FIG. 5 indicates the display screen after the stitch imaging has been already carried out once when the stitch imaging is supposed to be carried out a plurality of times. A stitched image 508 is displayed in the image area 501. Information about a subject A is displayed in the subject area 502. Image-capturing information 505a about the image-capturing site that is the entire lower limb, and image-capturing information 505b about the image-capturing site that is the entire spine are displayed in the image-capturing information area 503 as image-capturing information 505. The information about the image-capturing site, and the number of radiographic imaging units 102 used or to be used for the stitch imaging thereof are displayed side by side as the image-capturing information 505. The image-capturing information 505a is image-capturing information about the image-capturing that has been already carried out, and thumbnails of the radiographic images from the plurality of radiographic imaging units 102 are displayed therein while being arranged in a layout according to the layout relationship among the radiographic imaging units 102. In the example illustrated in FIG. 5, a thumbnail 506b of the radiographic image from the radiographic imaging unit 102b, a thumbnail 506c of the radiographic image from the radiographic imaging unit 102c, and a thumbnail 506a of the radiographic image from the radiographic imaging unit 102a are displayed while being arranged in this order. In this manner, the thumbnails are arranged based on the layout information, which allows the user to easily check whether the stitch imaging has been appropriately carried out. On the other hand, if there is an error in the layout information, this results in a failure to arrange the thumbnails appropriately, which allows the user to be notified of whether the layout information is appropriate in an easily understandable manner.

On the other hand, the image-capturing information 505b is image-capturing information about the image-capturing that is not yet carried out, and a display indicating the layout relationship among the plurality of radiographic imaging units 102 is presented therein instead of the thumbnails. In the example illustrated in FIG. 5, a display ("FPD B") 507b corresponding to the radiographic imaging unit 102b, a display ("FPD C") 507c corresponding to the radiographic imaging unit 102c, and a display ("FPD A") 507a corresponding to the radiographic imaging unit 102a are displayed while being arranged so as to be located at display positions according to the layout relationship among the radiographic imaging units 102a, 102b, and 102c. This display allows the user to check whether the radiographic imaging units 102a, 102b, and 102c are appropriately laid out on the touch panel monitor 108 of the control apparatus 104 before the image-capturing. The control apparatus 104 may be configured to cause the states of the radiographic imaging units 102a, 102b, and 102c to be displayed by the displays 507a, 507b, and 507c at this time.

The information indicating the states of the plurality of radiographic imaging units 102 is displayed in the state area 507. The radiographic imaging units 102 for which the information indicating the states is displayed there may be the radiographic imaging units 102 corresponding to the currently specified image-capturing condition. If the image-capturing condition corresponding to the stitch imaging is specified as illustrated in FIG. 5, the information indicating the states of the radiographic imaging units 102a, 102b, and 102c is displayed therein. In the state area 507, the pieces of information indicating the states of the plurality of radiographic imaging units 102 are displayed while being arranged on the display screen 500 at display positions according to the layout state among this plurality of radiographic imaging units 102. For example, if the radiographic imaging unit 102b and the radiographic imaging unit 102c are interchanged with the display screen displayed as illustrated in FIG. 5, this interchange results in a display of the respective states of the radiographic imaging units 102c, 102b, and 102a arranged in this order in the state area 507. Presenting the display in this manner allows the user to easily check the layout relationship among the plurality of radiographic imaging units 102.

The end button 504 is a button for ending an examination regarding the plurality of pieces of image-capturing information displayed on the display screen 500. If the end button 504 is pressed after an end of the image-capturing operations corresponding to all pieces of image-capturing information contained in this examination, this examination is ended. In this case, the CPU 401 generates the DICOM image file of the radiographic images regarding this examination, and causes the first NIC 405a to transmit this file to the PACS. On the other hand, if the end button 504 is pressed before the end of the image-capturing operations corresponding to the pieces of image-capturing information contained in this examination, this examination is set into a suspended state, and is stored into the storage unit 403 together with flag information indicating the suspended state.

The control apparatus 104 may be configured to cause the states of the individual radiographic imaging units 102 to be displayed in the displays 507a, 507b, and 507c, and cause readiness or unreadiness for the image-capturing to be clearly displayed in the state area 507 as a display indicating whether the stitch imaging can be carried out. In this case, the state area 507 is displayed in such a manner that a color of the state area 507 is, for example, grayed if even any one of the plurality of radiographic imaging units 102 is in the first state, i.e., is not in the state prepared for the acquisition of the radiographic image. Further, for example, a text "NOT READY" is displayed in addition thereto. The prohibition of the stitch imaging is clearly indicated by this display. On the other hand, if all of the plurality of radiographic imaging units 102 are in the second state prepared for the acquisition of the radiographic image, the color of the state area 507 is, for example, greened, and a text "READY" is displayed in addition thereto. The permission of the stitch imaging is clearly indicated by this display. In this manner, the display of the touch panel monitor 108 is controlled according to whether any one of the plurality of radiographic imaging units 102 is in the first state or all of the plurality of radiographic imaging units 102 are in the second state, by which the readiness or the unreadiness for the image-capturing is clearly indicated.

Figure 6:
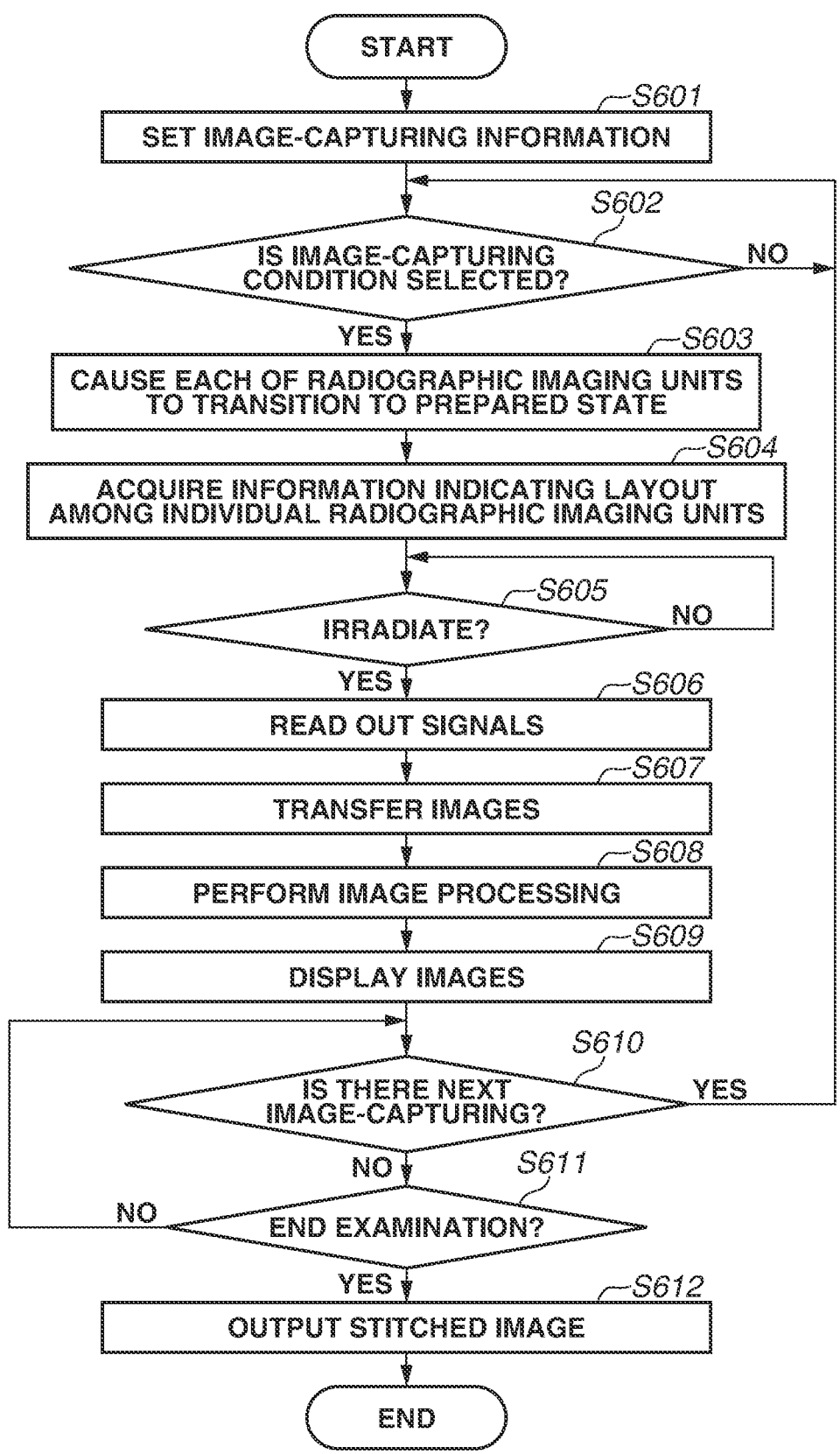
FIG. 6 is a flowchart illustrating a flow of processing regarding stitch imaging according to the exemplary embodiment.

A flow of processing regarding the stitch imaging according to the present exemplary embodiment will be described with reference to a flowchart illustrated in FIG. 6. A processing entity that performs the following processing is the CPU 401 of the control apparatus 104, unless otherwise noted specifically. The flow of the processing from steps S601 to S612 is controlled by the image-capturing control module 434.

In step S601, the CPU 401 sets one of pieces of image-capturing information (pieces of examination information) input from the RIS 151 as an examination target. In this process, for example, according to an operation input by which the user selects one of the plurality of pieces of examination information displayed in the form of a list, the CPU 401 sets this image-capturing information (the examination information) as the image-capturing target. At this time, for example, the CPU 401 executes the display control module 433 to cause the display screen 500 to be displayed on the display unit.

In step S602, the CPU 401 determines whether an operation input for selecting the image-capturing condition corresponding to the stitch imaging that is contained in the image-capturing information (the examination information) is entered. At this time, if the image-capturing information (the examination information) contains a plurality of image-capturing conditions, information corresponding to the plurality of image-capturing conditions is displayed in the image-capturing information area 503 on the display screen 500, and the CPU 401 determines whether an operation input for selecting one of them is entered by the user. If the operation input for the selection is not entered (NO in step S602), the determination process in step S602 is repeated. If the operation input for the selection is entered (YES in step S602), the processing proceeds to a next process. The processing may be configured to automatically proceed to step S603 regardless of the process of step S602, if the image-capturing information (the examination information) contains only one image-capturing condition.

In step S603, the CPU 401 specifies the image-capturing condition corresponding to the stitch imaging that has been selected by the operation input. Then, according to this specifying, the CPU 401 causes the second NIC 405b to transmit the signals for causing the states to transition to the prepared state to the plurality of radiographic imaging units 102a, 102b, and 102c involved in this stitch imaging. In response thereto, each of the radiographic imaging units 102a, 102b, and 102c apply the bias voltage to the two-dimensional image sensor 120 by the main control circuit 150 controlling the bias power source 140, if the bias voltage is not applied to the two-dimensional image sensor 120. After that, each of the radiographic imaging units 102a, 102b, and 102c carries out the initialization of reading out the image signals from the pixel array by the driving circuit 130 to read out dark current signals stored in the pixels. After an end of the initialization, each of the radiographic imaging units 102a, 102b, and 102c transmits, to the control apparatus 104, the state information indicating that each of the plurality of radiographic imaging units 102a, 102b, and 102c is in the second state, which is the state prepared for the acquisition of the radiographic image, after the completion of the initialization.

In step S604, the CPU 401 acquires the layout information indicating the layout relationship among the plurality of radiographic imaging units 102a, 102b, and 102c to be used for the stitch imaging. For example, in the case where the present processing is performed assuming that the stitch imaging system is a system such as the system illustrated in FIG. 1, the CPU 401 acquires the information indicating the respective communication paths of the plurality of radiographic imaging units 102a, 102b, and 102c from the relay 103. The relay 103 includes a plurality of physical ports to which the cables 205a, 205b, and 205c from the platform connectors 206a, 206b, and 206c respectively provided to the housing portions 201a, 201b, and 201c are connected. This relay 103 identifies which physical port each of the signals from the radiographic imaging units 102a, 102b, and 102c is input from, thereby generating the correspondence relationships between the physical ports and the radiographic imaging units 102a, 102b, and 102c, i.e., the information indicating the respective communication paths of the radiographic imaging units 102a, 102b, and 102c. The CPU 401 of the control apparatus 104 receives this information from the second NIC 405b. The CPU 401 acquires the information indicating the layout relationship from the information indicating the communication paths acquired in this manner.

Figure 5:
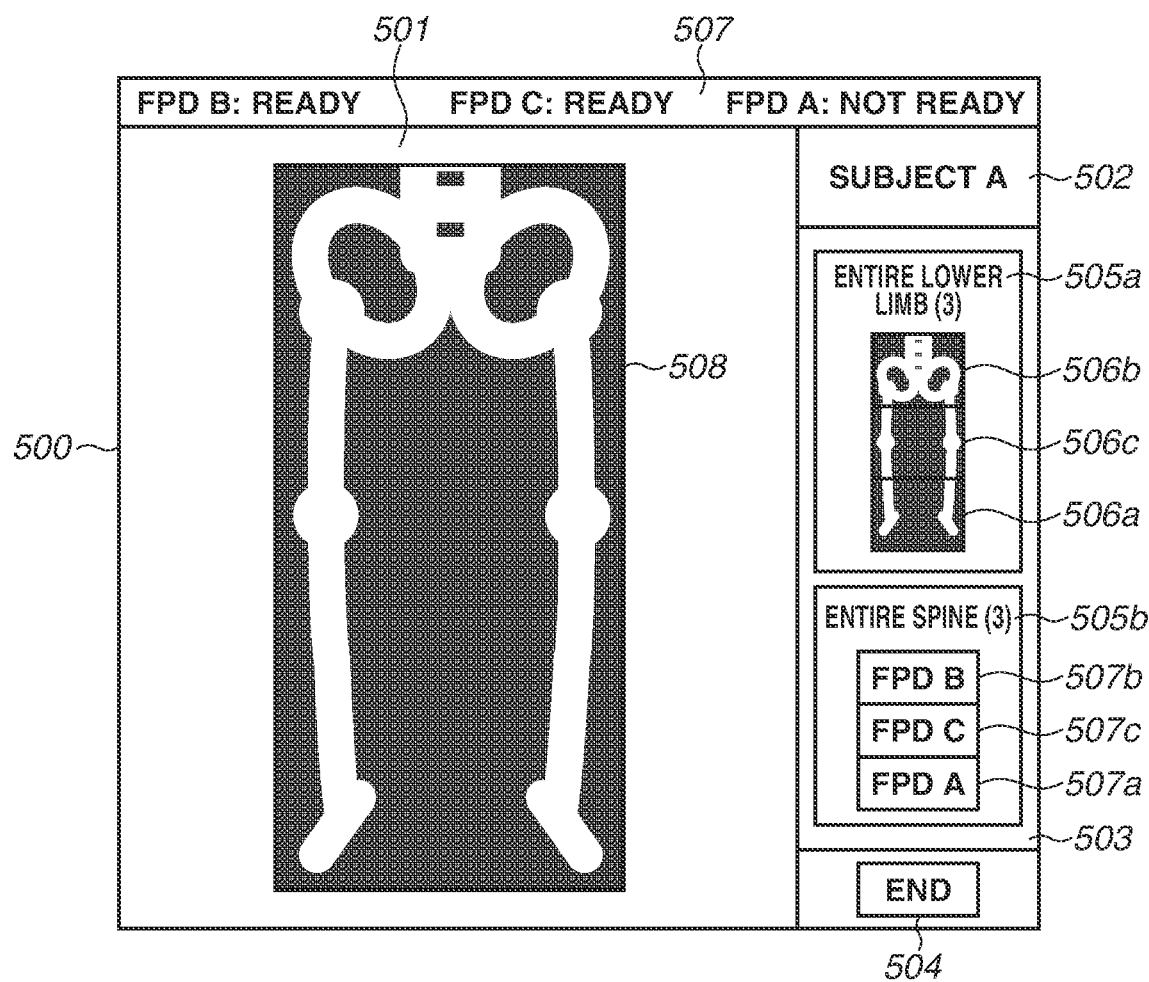
FIG. 5 illustrates an example of a display screen according to the exemplary embodiment.

As indicated by the image-capturing information 505b on the display screen 500 illustrated in FIG. 5, this information indicating the layout relationship is displayed as the information indicating the layout relationship among the plurality of radiographic imaging units 102a, 102b, and 102c to be used for the stitch imaging corresponding to this image-capturing information 505b.

In step S605, the CPU 401 determines whether the irradiation switch is pressed. If the irradiation switch is pressed (YES in step S605), the processing proceeds to step S606.

Whether the irradiation switch should be pressed is determined, for example, with use of the display based on the states of the plurality of radiographic imaging units 102a, 102b, and 102c displayed on the display screen 500. More specifically, the display of the specific area on the display screen 500 is controlled according to whether any one of the plurality of radiographic imaging units 102a, 102b, and 102c is in the first state or all of the plurality of radiographic imaging units 102a, 102b, and 102c are in the second state based on the state information acquired from each of the plurality of radiographic imaging units 102a, 102b, and 102c. This is as described in the description of the display screen 500 illustrated in FIG. 5.

In step S606, the driving circuit 130 of each of the radiographic imaging units 102a, 102b, and 102c reads out the image signals acquired by detecting the radiation with which the subject is irradiated by the readout circuit 170 to generate the digital radiographic image.

In step S607, the wired communication circuit 180 or the wireless communication circuit 160 of each of the radiographic imaging units 102a, 102b, and 102c transmits the generated digital radiographic image to the control apparatus 104. Each of the plurality of radiographic imaging units 102a, 102b, and 102c transmits the preview image small in data quantity and then transmits the image that contains the remaining data after that, thereby completing the transmission of the radiographic image acquired from the image-capturing. At this time, in a case where each of the radiographic imaging units 102a, 102b, and 102c transmits the radiographic image via the wired communication circuit 180, each of the radiographic imaging units 102a, 102b, and 102c employs the communication method that sequentially transmits the preview image and the image containing the remaining data in response to the readout of the image signals. This transmission is carried out asynchronously with the other radiographic imaging units 102. On the other hand, in a case where each of the radiographic imaging units 102a, 102b, and 102c transmits the images via the wireless communication circuit 160, each of the radiographic imaging units 102a, 102b, and 102c restricts the transmission of the image that contains the remaining data until the completion of the transmission of the preview images from all of the radiographic imaging units 102a, 102b, and 102c, in consideration of such a problem that this image transmission may weigh on the communication capacity.

In step S608, the CPU 401 of the control apparatus 104 performs the image processing on the plurality of radiographic images acquired from the plurality of radiographic imaging units 102a, 102b, and 102c with use of the GPU 406 and the like. This processing is, for example, the processing for generating the stitched image with use of the stitched image generation module 435, and the processing for reducing the number of structure images with use of the correction module 436. In the process of step S608, first, the CPU 401 performs the processing for acquiring a preview stitched image from the plurality of preview images, and then performs the processing for acquiring the stitched image from the plurality of radiographic images larger in data amount than these preview images after that. This processing is performed with use of the layout information acquired in step S604. The processing for reducing the number of structure images is performed on the radiographic image specified based on the layout information with use of the correction data prepared for the processing for reducing the number of structure images that is specified based on the layout information.

In step S609, the CPU 401 causes the preview stitched image and the stitched image acquired from the processing performed by the GPU 406 and the like to be displayed on the display unit.

In step S610, the CPU 401 determines whether there is an image-capturing condition on which the image-capturing is not yet carried out. If there is such an image-capturing condition (YES in step S610), the processing proceeds to step S602. Then, the CPU 401 performs the stitch imaging based on the new image-capturing condition. If there is no image-capturing condition on which the image-capturing is not yet carried out (NO in step S610), then in step S611, the CPU 401 determines whether to end the examination. If the CPU 401 does not end the examination (NO in step S611), the CPU 401 performs processing for waiting for an addition of an image-capturing condition on which the image-capturing is not yet carried out, or an instruction to end the examination. If the examination end button 504 is pressed at this time (YES in step S611), the CPU 401 ends the examination. In step S612, the CPU 401 causes the first NIC 405a to output the DICOM image file of the stitched image to the PACS. With this output, the examination that contains the stitch imaging is ended.

In the above-described example, the stitch imaging system is assumed to carry out the stitch imaging a plurality of times during a single examination. However, it is not limited thereto, and it may be assumed to carry out the stitch imaging together with image-capturing using a different image-capturing method from the stitch imaging during a single examination. In this manner, in the case of the imaging system capable of carrying out the stitch imaging, when carrying out the stitch imaging, the control apparatus 104 transmits the signals for causing the states of the plurality of radiographic imaging units 102a, 102b, and 102c to transition according to the specifying of the image-capturing condition. On the other hand, when carrying out the image-capturing using the single radiographic imaging unit 102, such as normal image-capturing, the control apparatus 104 transmits the signal for causing the state of this single radiographic imaging unit 102 to transition according to the specifying of the image-capturing condition. Further, when carrying out the stitch imaging, the control apparatus 104 controls the display based on the state information acquired from each of the plurality of radiographic imaging units 102a, 102b, and 102c according to whether any one of the plurality of radiographic imaging units 102a, 102b, and 102c is in the first state or all of the plurality of radiographic imaging units 102a, 102b, and 102c are in the second state. When carrying out the image-capturing using the single radiographic imaging unit 102, the control apparatus 104 causes the information indicating the state of this single radiographic imaging unit 102 to be displayed.

Further, when carrying out the stitch imaging, the control apparatus 104 acquires the layout information indicating the layout relationship among the plurality of radiographic imaging units 102a, 102b, and 102c. The radiographic image(s) acquired from at least one of the radiographic imaging unit(s) 102 specified based on this layout information is or are corrected based on the correction data specified based on the layout information.

Further, at the time executing the stitch imaging, the control is performed so as to restrict the transmission of the image according to the communication of the other radiographic imaging units 102 in consideration of the problem that the image transmission may weigh on the communication capacity. On the other hand, at the time of the image-capturing using the single radiographic imaging unit 102, the image that contains the remaining data is transmitted according to the end of the transmission of the preview image because priority is placed on transmitting the image as quickly as possible in this case.

Figure 7:
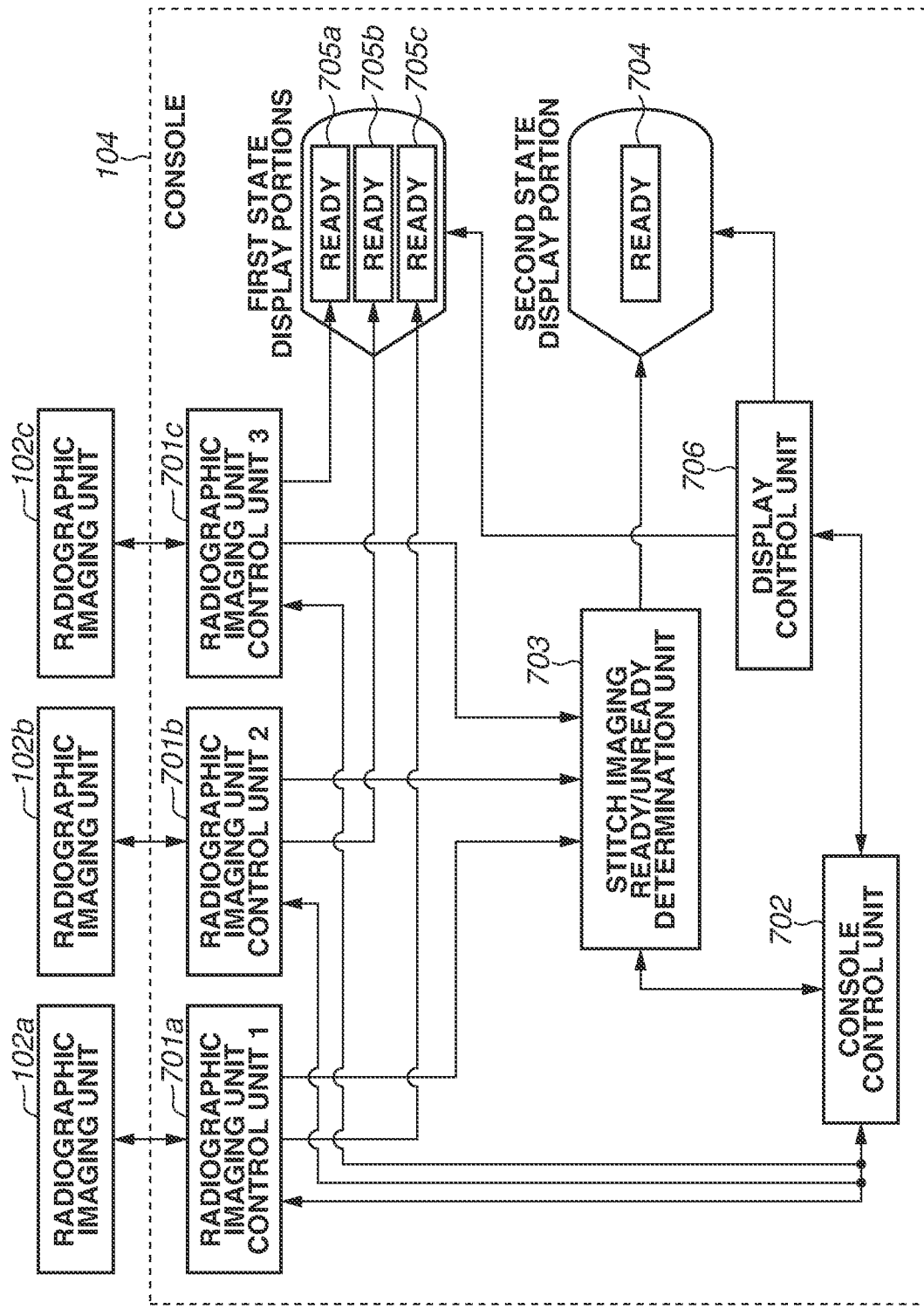
FIG. 7 is a block diagram illustrating functions included in the control apparatus according to the exemplary embodiment.

The functions of the control apparatus 104 according to the present exemplary embodiment will be described with reference to FIG. 7. The radiographic imaging units 102a, 102b, and 102c, and the control apparatus 104 are connected to each other via a wired or wireless network, or a dedicated line. The radiographic imaging units 102a, 102b, and 102c captures X-rays generated by the radiation generation unit 100. The control apparatus 104 is provided with an application that includes a user interface operable on the computer and outputs an image and a graphical user interface (GUI) onto the touch panel monitor 108 while controlling the operations of the radiographic imaging units 102a, 102b, and 102c.

The image data captured by the radiographic imaging units 102a, 102b, and 102c is subjected to the image processing performed by the control apparatus 104, and is displayed on the touch panel monitor 108. Then, generally, the image data is output outwardly via a not-illustrated network.

The control apparatus 104 includes first, second, and third radiographic imaging unit control units 701a, 701b, and 701c, a console control unit 702, a stitch imaging ready/ unready determination unit (a determination unit) 703, and a display control unit 706. The first, second, and third radiographic imaging unit control units 701a, 701b, and 701c, and the display control unit 706 correspond to the image-capturing module 434, and the display control module 433 illustrated in FIG. 4, respectively. The determination unit 703 and the console control unit 702 correspond to the communication control module 432 and the image-capturing module 434. First state display portions 705 (705a, 705b, and 705c) and a second state display portion 704 indicate the specific display area on the display screen 500 displayed on the touch panel monitor 108. In the example illustrated in FIG. 7, the first state display portions 705 and the second state display portion 704 are included in the control apparatus 104, but the display unit, such as the touch panel monitor 108, may be provided as an apparatus independent of the control apparatus 104 as illustrated in FIGS. 1 and 2.

The determination unit 703 makes a first determination, which determines that any one of the plurality of radiographic imaging units 102a, 102b, and 102c is in the first state, and a second determination, which determines that all of the plurality of radiographic imaging units 102a, 102b, and 102c are in the second state, based on the state information from each of the plurality of radiographic imaging units 102a, 102b, and 102c. As used herein, the first state refers to the state of each of the plurality of radiographic imaging units 102a, 102b, and 102c that is not the state prepared for the acquisition of the radiographic image. Further, the second state refers to the state prepared for the acquisition of the radiographic image. This state information is received from the radiographic imaging units 102a, 102b, and 102c as described above.

The display control unit 706 controls the display on the touch panel monitor 108 according to whether a result of the determination by the determination unit 703 is the first determination or the second determination.

The console control unit 702 controls the communication, the operation of the control apparatus (a console) 104, such as management of the examination information (the image-capturing information, such as the image-capturing condition), data processing, the image processing, and the like.

FIG. 11A illustrates one example of an image-capturing screen GUI (the display screen 500) that the control apparatus 104 according to the present exemplary embodiment displays on the touch panel monitor 108. Components displayed on the display screen 500 include a state area 1101 where the state of the radiographic imaging unit 102a (102b, 102c) is displayed, the image area where the captured image acquired from the radiographic imaging unit 102a (102b, 102c) is displayed, the subject area 502 where the subject information corresponding to the ongoing examination is displayed, the image-capturing information area 503 where an image-capturing list, a thumbnail of the image already captured, and the like are displayed, and the end button 504 for instructing the stitch imaging system to end the examination. These GUIs are as described in the description of FIG. 5. The stitched image acquired from the stitch imaging is displayed in the image area.

A display in a first display mode is presented in the state area 1101, if at least one of the plurality of radiographic imaging units 102a, 102b, and 102c is in the first state. The display in the first display mode is a display indicating that the radiographic imaging unit(s) 102 is or are unprepared, so that the irradiation with the radiation is not permitted. For example, the text "NOT READY (UNPREPARED)" is displayed in the state area 1101. Besides that, the display control unit 706 may be configured to gray or black the state area 1101 or cause an X mark to be displayed in the state area 1101. This display may be referred to as a NOT-READY display. On the other hand, a display in a second display mode is presented in the state area 1101, if all of the plurality of radiographic imaging units 102a, 102b, and 102c are in the second state. The display in the second display mode is a display indicating that the radiographic imaging units 102a, 102b, and 102c are prepared, so that the irradiation with the radiation is permitted. For example, the text "READY (PREPARED)" is displayed in the state area 1101. Besides that, the display control unit 706 may be configured to green or blue the state area 1101 or cause a circle mark to be displayed in the state area 1101. This display may be referred to as a READY display.

The display control unit 706 may be configured to present the above-described state display based on not only the state of the radiographic imaging unit 102a but also a state of the control apparatus (the console control unit 702) 104, and a state of the radiation generation unit 100 if the control apparatus 104 communicates with the radiation generation unit 100. For example, as the state of the console control unit 702, the display control unit 706 displays that the image-capturing is not permitted if the console control unit 702 is in a first status, in which any one of the image-capturing condition and the subject information is not specified. This is because receiving the radiographic image in this first status may result in an inability to identify the subject information or the image-capturing condition that should be associated with this radiographic image. On the other hand, the display control unit 706 displays that the image-capturing is permitted if the console control unit 702 is in a second status, in which the image-capturing condition and the subject information are specified. As the state of the radiation generation unit 100, the display control unit 706 may be configured to display that the image-capturing is not permitted if the radiation generation unit 100 is in a first status, in which the radiation irradiation unit 100a is not powered on or an irradiation condition is not specified, and display that the image-capturing is permitted if the radiation generation unit 100 is in a second status, in which the radiation irradiation unit 100a is powered on and the irradiation condition is specified.

Then, the display control unit 706 presents the display in the state area 1101 in the second display mode, if all of the states of the radiographic imaging units 102a, 102b, and 102c, and the state of the control apparatus 104 or the radiation generation unit 100 are in the state that permits the image-capturing. Controlling the display in this manner allows the user to determine whether the image-capturing is permitted only by viewing the display in the state area 1101, thereby reducing a mistake such as erroneously pressing the switch for irradiating the subject with the X-rays.

Display processing according to the present exemplary embodiment will be described with reference to a flowchart illustrated in FIG. 8.

In step S801, the stitch imaging ready/unready determination unit 703 determines whether the image-capturing to be carried out next is the stitch imaging. The console control unit 702 has a list of examinations currently in process, and performs control in such a manner that the stitch imaging system sequentially captures images that are not yet captured. Upon a selection of an image to be captured next, the stitch imaging ready/unready determination unit 703 determines whether this image-capturing is the stitch imaging. If the image-capturing to be carried out next is the stitch imaging (YES in step S801), possible methods therefor include a method that images the subject by using the plurality of radiographic imaging units 102 simultaneously and irradiating the subject with the X-rays once, and then combines the resultant images, and a method that images the subject by irradiating the subject with the X-rays separately for each of the images to capture the images one by one, and then combines the resultant images. In the present exemplary embodiment, the stitch imaging ready/unready determination unit 703 determines whether the image-capturing condition set to the image to be captured next is the condition corresponding to the image-capturing that images the subject by irradiating the subject with the X-rays once. The image that is intended to be captured by the stitch imaging should be provided with information useful for this determination preset thereto, thereby allowing this image to be identified in terms of whether the stitch imaging is intended therefor only from reference to the image-capturing condition. Examples of such information include the number of radiographic imaging units to be used that is set to a plural number.

If the radiographic imaging unit(s) 102 is or are not in the state capable of image-capturing at this stage, the NOT-READY display is presented in the state area 507. Even if the radiographic imaging unit(s) 102 is or are in the state capable of image-capturing, the NOT-READY display is presented unless the console control unit 702 is prepared for the image-capturing. The NOT-READY display at this time is presented in the following steps. If the image-capturing to be carried out next is determined to be the stitch imaging as a result of the determination determining whether this image-capturing is the stitch imaging (YES in step S801), the processing proceeds to step S803. If the image-capturing to be carried out next is determined to be not the stitch imaging as a result of this determination (NO in step S801), the processing proceeds to step S802.

In step S802, the display control unit 706 displays the state of the radiographic imaging unit 102. The console control unit 702 controls the radiographic imaging unit 102 via the radiographic imaging unit control unit 701 according to the result determined by the stitch imaging ready/unready determination unit 703 in step S801. If the image-capturing to be carried out next is not the stitch imaging (NO in step S801), since this image-capturing is normally performed by the method that images the subject with use of one radiographic imaging unit 102, the display control unit 706 displays the state of the corresponding radiographic imaging unit 102 in the state area 507. This state is being updated according to a change in the state of the radiographic imaging unit 102.

In step S803, the console control unit 702 issues a READY request to each of the radiographic imaging units 102 to be used. In this case, the image-capturing to be carried out next is performed by the method that images the subject by irradiating the subject with the X-rays once with use of the plurality of radiographic imaging units 102. Therefore, the console control unit 702 controls the plurality of radiographic imaging units 102 that are supposed to image the subject, to transition the states thereof to the state ready for the irradiation. As the control of the radiographic imaging units 102, the console control unit 702 controls the radiographic imaging unit 102a (102b, 102c) via the radiographic imaging unit control unit 701a (701b, 701c). Normally, the radiographic imaging units 102 are brought into a state incapable of the image-capturing after carrying out the image-capturing, and therefore should be controlled so as to return to the state capable of the image-capturing. On the other hand, the radiographic imaging units 102 may automatically return to the state capable of the image-capturing again after carrying out the image-capturing depending on the system configuration. In this case, the radiographic imaging units 102 do not have to be controlled to return to the state capable of image-capturing. However, the console control unit 702 side may fail to be brought into the state capable of receiving the image-capturing, whereby the console control side is controlled so as to be brought into the state capable of image-capturing in this case. In either case, the READY display is not presented in the state area 507 unless both of the radiographic imaging units 102 and the console control unit 702 are brought into the state capable of image-capturing.

In step S804, the control apparatus 104 checks a result of the READY request. If having issued the instruction to instruct the radiographic imaging unit 102a (102b, 102c) to transition to the state capable of image-capturing, the control apparatus 104 checks whether the transition to the state capable of image-capturing can be ensured. There are several possible methods for checking that, and any of them can be realized by a known technique.

In step S805, the control apparatus 104 determines whether all of the radiographic imaging units 102 to be used are ready. If all of the radiographic imaging units 102 are confirmed to be in the state capable of image-capturing as a result of the issue of the READY request in step S804 (YES in step S805), the processing proceeds to step S807. If any one of the radiographic imaging units 102 (102a, 102b, 102c) is not in the ready state (NO in step S805), the processing proceeds to step S806. The processing also proceeds to step S806 if the console control side is not in the state capable of image-capturing.

In step S806, the display control unit 706 presents the NOT-READY display. Since it is found out as a result of step S805 that there is eat least one radiographic imaging unit 102 that is not in the ready state among the radiographic imaging units 102 to be used for the stitch imaging, irradiating the subject with the X-rays in this state leads to a failure to form an image of a portion corresponding to the radiographic imaging unit 102 that is not in the ready state, resulting in invalid exposure. Therefore, the display control unit 706 causes the NOT-READY display to be presented in the state area 507.

If a state change occurs regarding the state capable of the image-capturing from the radiographic imaging unit side in this state, the processing proceeds to step S804 again. Similarly, the processing also proceeds to step S804 if a state change occurs in the state capable of image-capturing on the console control side.

In step S807, the display control unit 706 presents the READY display. Since all of the radiographic imaging units 102 to be used for the image-capturing are in the state capable of image-capturing, the display control unit 706 displays the information indicating the readiness in the state area 507 as the second state display portion 704.

If a state change occurs regarding the state capable of image-capturing from the radiographic imaging unit side in this state, the processing proceeds to step S804 again. Similarly, the processing also proceeds to step S804 if a state change occurs in the state capable of image-capturing on the console control side.

Display processing according to another exemplary embodiment will be described with reference to a flowchart illustrated in FIG. 9. In this processing, steps S901 and S902 are similar to steps S801 and S802 in the example illustrated in FIG. 8, respectively. Further, the processing of step S906 and subsequence steps is similar to the processing of step S803 and the subsequent steps illustrated in FIG. 8, so that a description thereof will be omitted. In the example illustrated in FIG. 9, the state area 1101 is divided into areas 1106, 1107, and 1108 that indicate the respective states of the radiographic imaging units 102a, 102b, and 102c.

In step S903, the control apparatus 104 identifies the radiographic imaging units 102 to be used. The radiographic imaging units 102 to be used are defined in a setting of the image-capturing condition in advance. Examples of such a condition include the type of the radiographic imaging unit 102, whether the image-capturing will use two radiographic imaging units 102 or three radiographic imaging units 102, and which orientation the image-capturing should be carried out in, a portrait orientation or a landscape orientation of the radiographic imaging unit 102.

In step S904, the control apparatus 104 determines whether the radiographic imaging units 102 to be used are in the connected state. Normally, the console control unit 702 manages the states of the connected radiographic imaging units 102, and is configured to be able to detect whether the radiographic imaging units 102 are in the connected state, whether the radiographic imaging units 102 are in the state capable of image-capturing, and the like. In a case where the console control unit 702 does not manage the states of the radiographic imaging units 102, the control apparatus 104 recognizes the states by, for example, inquiring to recognize the states. Upon recognizing the respective states of the radiographic imaging units 102, the control apparatus 104 determines whether the radiographic imaging units 102 are in the connected state or in the unconnected state. If all of the radiographic imaging units 102 are in the connected state (YES in step S904), the processing proceeds to step S906. If there is at least one radiographic imaging unit 102 in the unconnected state (NO in step S904), the processing proceeds to step S905.

In step S905, the display control unit 706 displays that the radiographic imaging unit(s) 102 is or are in the unconnected state. Because of the presence of the radiographic imaging unit(s) 102 in the unconnected state, the display control unit 706 displays the second state display portion 704 of the radiographic imaging units 102 that indicates the NOT-READY state as the unconnected state in the state area 507. If a state change occurs in the connection states of the radiographic imaging units 102 to be used, the processing proceeds to step S904. Step S906 and the subsequent steps are similar to step S803 and the subsequent steps illustrated in FIG. 8, and therefore descriptions thereof will be omitted.

In one exemplary embodiment, the colors of the areas 1106, 1107, and 1108 are changed according to whether any one of the plurality of radiographic imaging units 102 is in the above-described first state or all of the plurality of radiographic imaging units 102 are in the above-described second state. For example, the areas 1106, 1107, and 1108 are grayed if the image-capturing cannot be permitted, and are greened if the image-capturing can be permitted. Displaying the areas 1106, 1107, and 1108 in this manner allows whether the image-capturing can be carried out to be displayed in a manner easily understandable to the user.

Display processing according to another exemplary embodiment will be described with reference to a flowchart illustrated in FIG. 10. Steps S1001 to S1005 are similar to the example illustrated in FIG. 9.

In step S1006, the control apparatus 1004 collects status information (the information indicating the states) of the radiographic imaging units 102 to be used. Normally, the console control unit 702 manages the information. Examples of the status information include information indicating a temperature of the radiographic imaging unit 102, information indicating whether the radiographic imaging unit 102 is driven by a battery, information indicating a remaining capacity of the battery if the radiographic imaging unit 102 is driven by the battery, and information about radio waves if the radiographic imaging unit 102 communicates wirelessly. Besides them, the examples of the status information include the state of the radiographic imaging unit 102 such as the state capable of image-capturing and an error state, and the state connected or unconnected to the console.

In step S1007, the control apparatus 104 determines whether the collected statuses are information that should be treated as a logical product or information that should be treated as a logical sum, if the images are collected by the plurality of radiographic imaging units 102 with the subject irradiated with the X-rays once. For example, the state capable of image-capturing is treated as the logical product, because the image-capturing should be prohibited if there is even one radiographic imaging unit 102 that is not ready for the image-capturing. In other words, the READY display is presented in the second state display only if all of the radiographic imaging units 102 are in the state capable of image-capturing. The NOT-READY display is presented in the second sate display if even only one of the radiographic imaging units 102 is not in the state capable of image-capturing. For example, suppose that displays defined as the battery status include a display 1201 indicating that the battery is in a fully charged state, i.e., a level 3, a display 1202 indicating that the battery is in a state of level 2 downgraded from the fully charged state by one level, a display 1203 indicating that the battery is in a state of level 1, and a display 1204 indicating that the battery is in a state of level 0. If the battery states of the plurality of radiographic imaging units 102a, 102b, and 102c are the level 3, the level 3, and the level 3, respectively, the level 3, i.e., the display 1201 is displayed as the battery status. If the battery states of the radiographic imaging units 102a, 102b, and 102c are the level 3, the level 2, and the level 1, respectively, the level 1, i.e., the display 1203 is displayed as the battery status. In other words, the display control unit 706 is assumed to cause the state of the radiographic imaging unit 102 in the worst battery state to be displayed, and is assumed to, if there is even one radiographic imaging unit 102 in a low level state, present a display corresponding to this low level. The information about radio waves is also displayed in a similar manner. Assuming that a radio field intensity is expressed by a plurality of levels, a low status is adopted if there is even one radiographic imaging unit 102 in a low level state.

In step S1008, the display control unit 706 presents the status display treated as the logical sum. As one example thereof, the display control unit 706 displays the battery status in a second information display portion as the low status, if there is even one radiographic imaging unit 102 in the battery state that is a status of a low level. If a state change occurs in the displayed status, the processing proceeds to step S1006.

In step S1009, the display control unit 706 presents the status display treated as the logical product. As one example thereof, the display control unit 706 does not display that the image-capturing can be carried out unless the conditions of all of the radiographic imaging units 102 satisfy the state capable of image-capturing. In other words, the display control unit 706 presents the READY display in the second information display portion only when all of the radiographic imaging units 102 are in the state capable of image-capturing. The connection/disconnection status is also displayed in a similar manner. If a state change occurs in the displayed status, the processing proceeds to step S1006.

Figure 8:
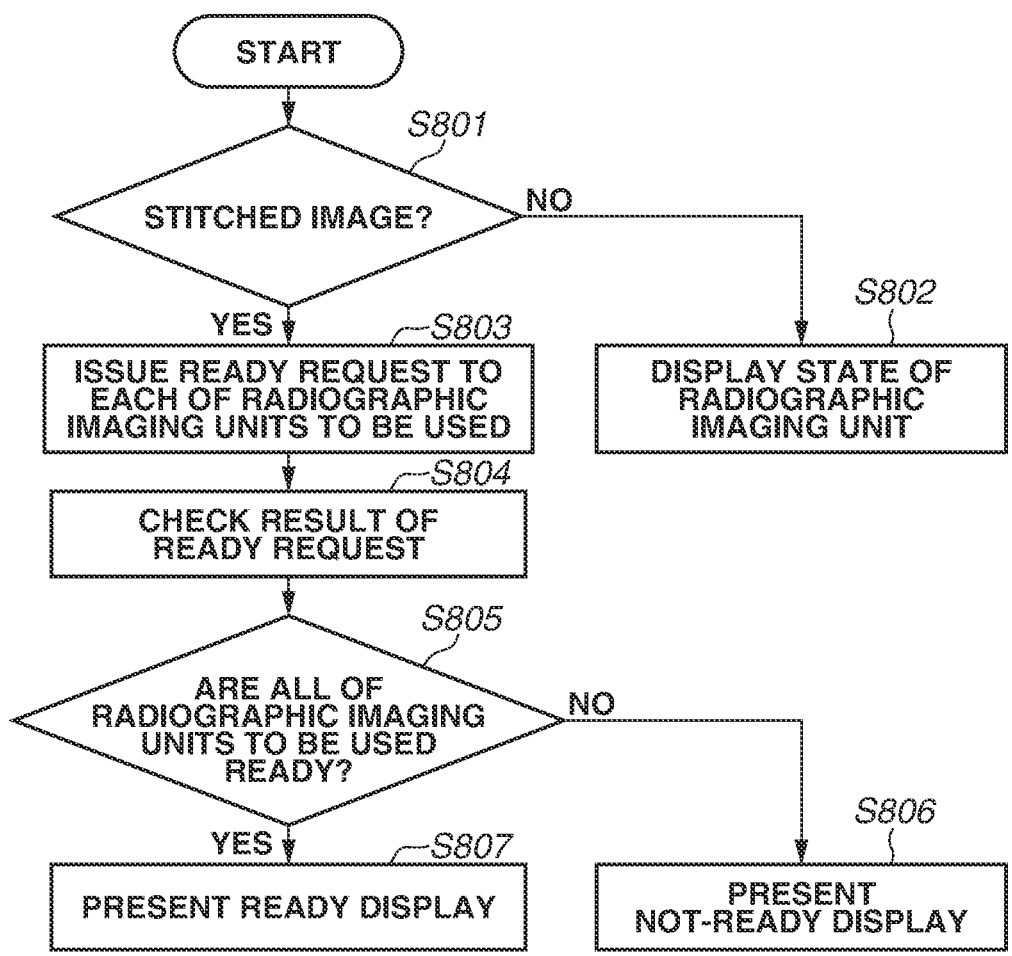
FIG. 8 is a flowchart illustrating a flow of display processing according to the exemplary embodiment.
Figure 9:
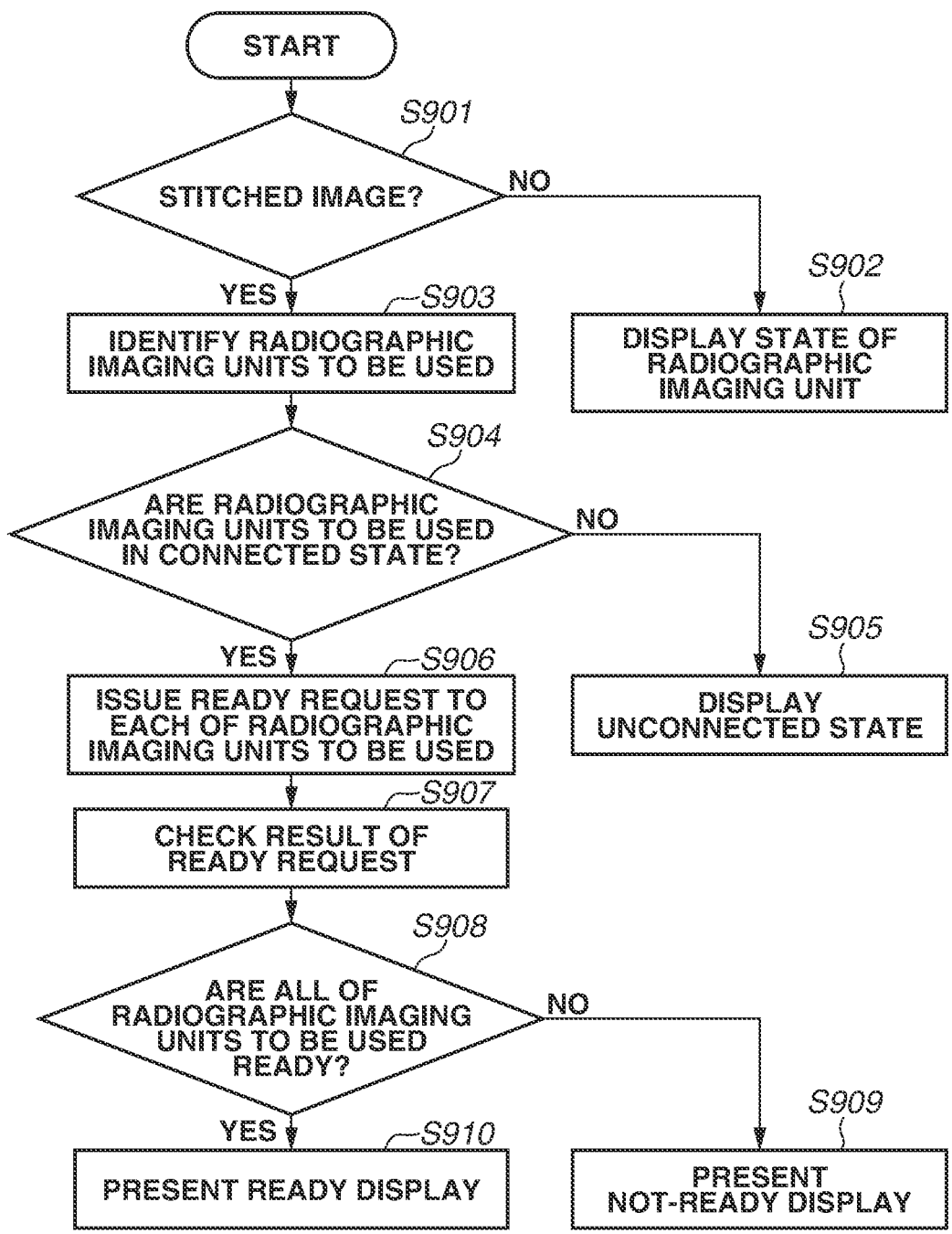
FIG. 9 is a flowchart illustrating a flow of display processing according to another exemplary embodiment.
Figure 10:
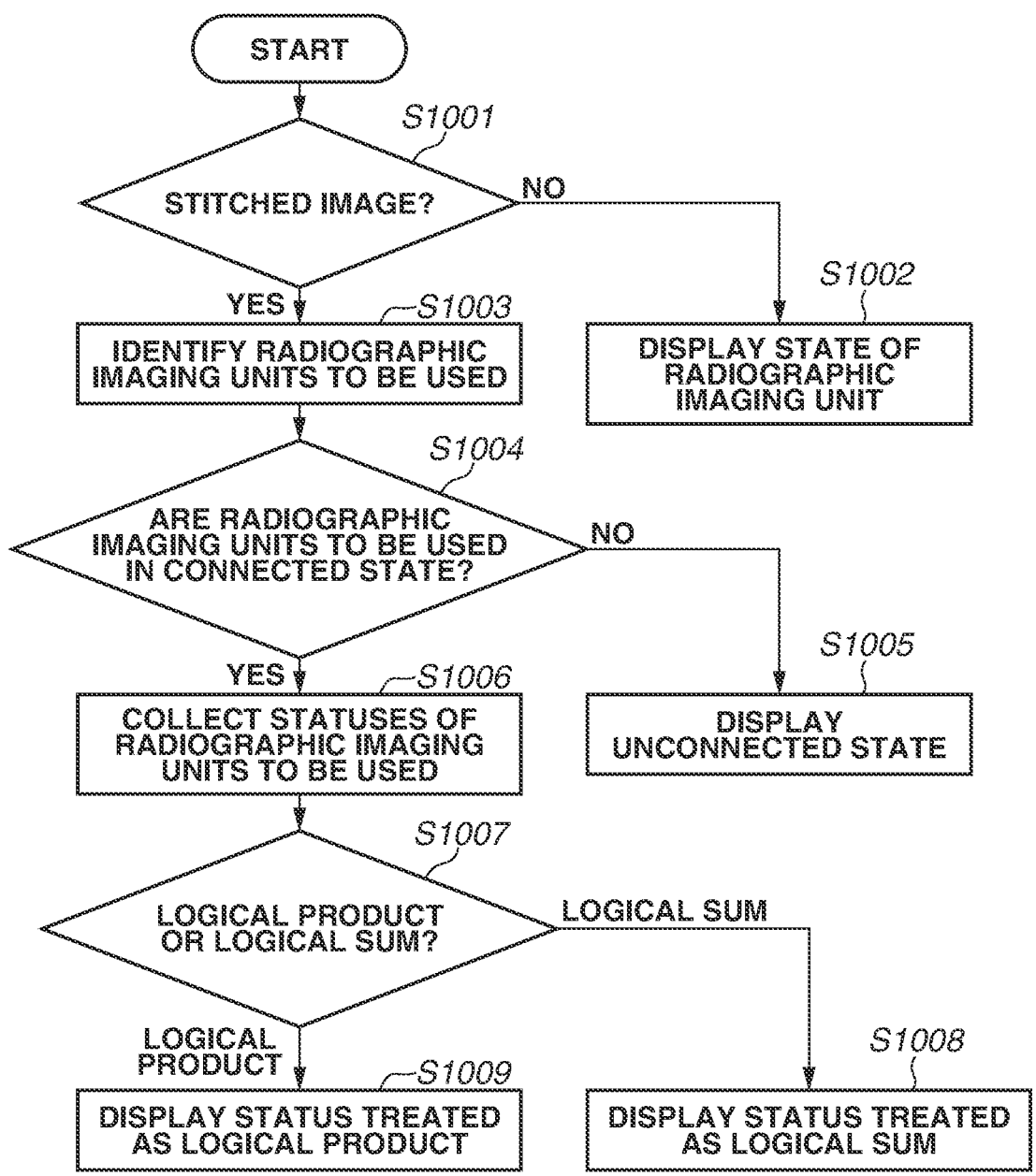
FIG. 10 is a flowchart illustrating a flow of display processing according to another exemplary embodiment.

In the examples illustrated in FIGS. 8 to 10, if the image-capturing to be carried out next is determined to be the stitch imaging in step S801, S901, S1001, or the like, the display control unit 706 displays the second state display portion 704 in the image area as the display in the state area 507. If the image-capturing to be carried out next is determined to be not the stitch imaging, since this image-capturing is normally to be carried out with use of one radiographic imaging unit 102, therefore, the display control unit 706 displays the status regarding any active radiographic imaging unit 102 among the first state display portions 705a, 705b, and 705c in the image area. In this case, both of these displays are presented in the same image area.

In another exemplary embodiment, the display control unit 706 displays the first state display portions 705 in the image area even if the image-capturing to be carried out next is the stitch imaging. For example, if any of the radiographic imaging units 102 is not in the state capable of image-capturing or there is an unconnected radiographic imaging unit 102, the display control unit 706 presents the first state display, thereby displaying the respective states of the radiographic imaging units 102. An example illustrated in FIG. 11B is one example of a GUI in which the first state display is presented in the state area 507 although the image-capturing to be carried out next is the stitch imaging. For example, the state of the radiographic imaging unit 102a, the state of the radiographic imaging unit 102b, and the state of the radiographic imaging unit 102c are displayed in the area 1106, the area 1107, and the area 1108, respectively.

Figure 11C:
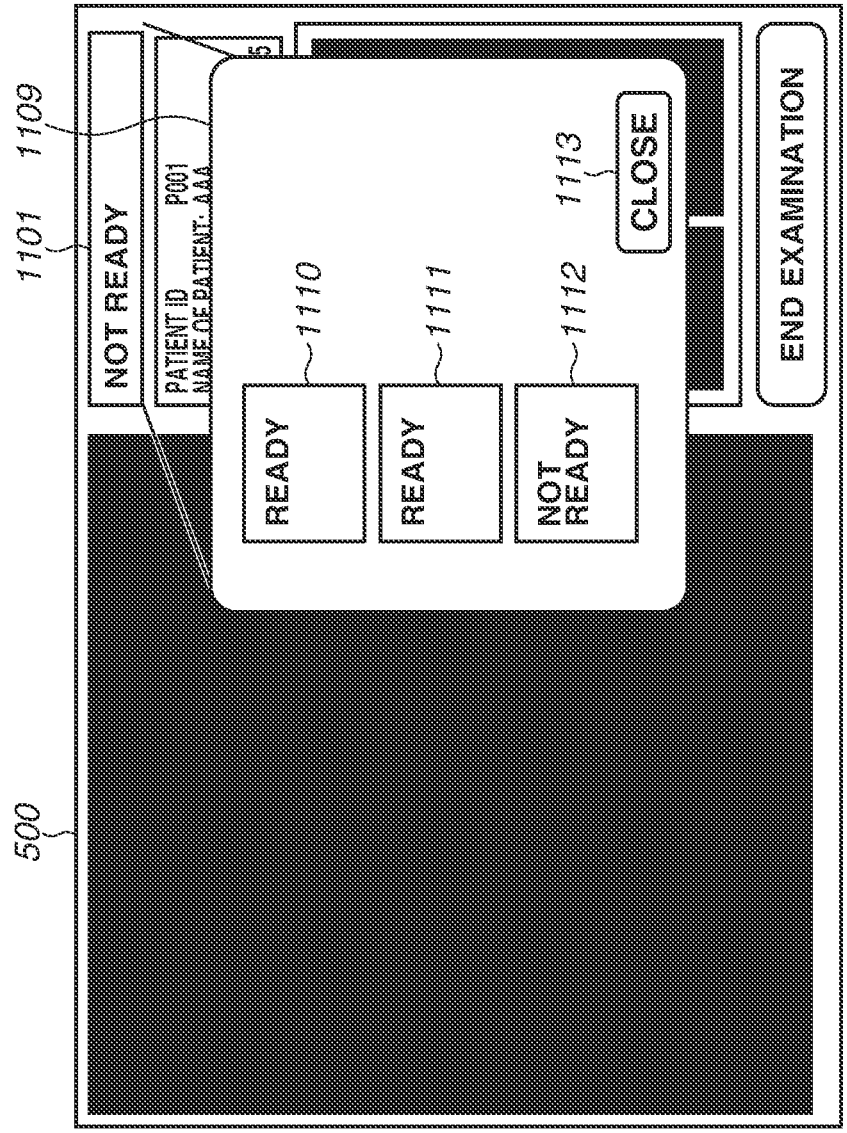
Figure 12:
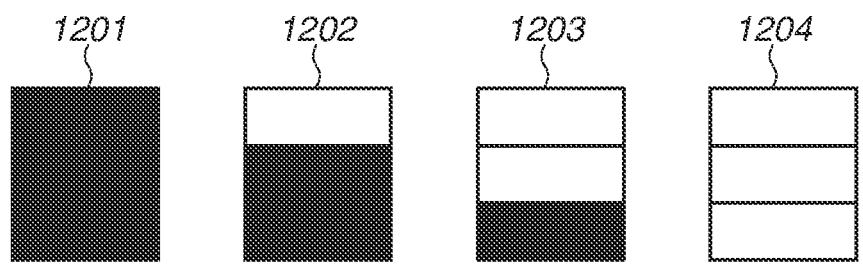
FIG. 12 illustrates an example of a display of states of a plurality of radiographic imaging units according to the other display unit.

The display control unit 706 may switch these displays by dynamically switching them. More specifically, the display control unit 706 may switch the displays when the processing proceeds to step S806 as a result of the process of step S805, when the processing proceeds to step S905 as a result of the process of step S904, and when the processing proceeds to step S909 as a result of the process of step S908. The display control unit 706 dynamically switches the first state display and the second state display in the above-described example, but may switch them according to a user's action. For example, the display control unit 706 switches the displays in the following manner. The display control unit 706 normally presents the second state display according to the user's inputting some action, as illustrated in FIG. 11C. Then, the display control unit 706 displays a display area 1109 or the like that is different therefrom. This display area 1109 contains areas 1110, 1111, and 1112 for the first state display therein, so that the display control unit 706 displays the first display state portions 705*a*, 705*b*, and 705*c* in the areas 1110, 1111, and 1112, respectively.

Further, the system can also be constructed so as to be able to constantly present the first state display and the second state display. For example, an area where the first state display is presented, and an area where the second state display is presented are provided separately, as illustrated in FIG. 11D. In this case, the first state display is presented in areas 1114, 1115, and 1116. Further, the second state display is presented in the state area 1101.

In this manner, in one exemplary embodiment, the information indicating that the irradiation can be carried out is displayed when all of the radiographic imaging units 102 are prepared for the image-capturing, which brings about an effect of preventing erroneous exposure. Especially, in a case where the radiographic imaging units 102*a*, 102*b*, and 102*c* and the radiation generation unit 100 do not communicate with each other, the radiation detection unit 100 can irradiate the subject with the radiation regardless of the states of the radiographic imaging units 102*a*, 102*b*, and 102*c* by pressing the irradiation switch. In such a case, it is important to display whether the image-capturing can be carried out from the point of view of preventing the erroneous exposure, and it is significant to display the prohibition of the image-capturing until all of the radiographic imaging units 102 are prepared for the image-capturing.

Further, if there is a radiographic imaging unit 102 in the unconnected state, the stitch imaging system can never establish the state capable of the image-capturing, and therefore skips the processing for causing the radiographic imaging units 102 to transition to the state capable of irradiation. This brings about an effect of allowing the stitch imaging system to become operable without requiring the user to spend an unnecessary waiting time and the like. In still another exemplary embodiment illustrated in FIG. 9, the status display is presented while adopting a state that requires the user to be alarmed and prompted to take some action, which brings about an effect of reducing an operation mistake, inadvertent omission of an operation, and the like. In still another exemplary embodiment illustrated in FIG. 10, the user can operate the stitch imaging system while checking similar user interfaces between the stitch imaging and other imaging, which brings about an effect of allowing the user to operate the stitch imaging system with a consistent operation feeling. Further, in another exemplary embodiment, the user can also be aware of an abnormal state of the individual radiographic imaging unit 102, which brings about an effect of improving operability for the user.

In the above-described exemplary embodiments, the radiographic imaging units 102*a*, 102*b*, and 102*c* are each assumed to transmit the preview image smaller in data amount than the radiographic image acquired from the image-capturing, and then transmit the image that contains the remaining data (the entire image or the second to fourth reduced images) after that, but are not limited thereto. For example, the radiographic imaging units 102*a*, 102*b*, and 102*c* may be each configured to transmit the radiographic image without generating the preview image.

The control apparatus 104 in the above-described exemplary embodiments is a single apparatus. However, in another exemplary embodiment, the functions of this control apparatus 104 are realized by a control system including a plurality of information processing apparatuses. In this case, the plurality of information processing apparatuses each includes a communication circuit, and is communicable with one another by this communication circuit. One of the plurality of information processing apparatuses can be configured to function as an image processing unit that generates the stitched image, and another apparatus can be configured to function as a control unit. The plurality of information processing apparatuses only has to be communicable at a predetermined communication rate, and does not have to be set up in a same hospital facility or a same country. Further, this control system can also be configured to use, for example, a server apparatus or a server group shared among a plurality of control systems as the image processing unit.

Further, exemplary embodiments of the present invention also include an exemplary embodiment in which a program of software capable of realizing the functions of the above-described exemplary embodiments is supplied to a system or an apparatus, and a computer of this system or apparatus reads out and executes a code of this supplied program.

Therefore, the program code itself installed in this computer for realizing the processing according to the exemplary embodiments by the computer is also one exemplary embodiment of the present invention. Further, an operating system (OS) or the like running on the computer partially or entirely performs the actual processing based on an instruction contained in the program read out by the computer, and the functions of the above-described exemplary embodiments can also be realized by this processing.

An exemplary embodiment constructed by arbitrarily combining the above-described exemplary embodiments is also included in exemplary embodiments of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An information processing apparatus configured to connect communicatively with a plurality of radiographic imaging units for stitch imaging, the information processing apparatus comprising:
   a memory storing a program; and
   one or more processors which, by executing the program, function as:
   a display control unit configured to individually display, for each of the plurality of radiographic imaging units, information which indicates whether or not the each of the plurality of radiographic imaging unit is in a state prepared for generating an image.

2. The information processing apparatus according to claim 1, wherein the display control unit displays the information in a layout according to a layout relationship among the plurality of radiographic imaging units.

3. The information processing apparatus according to claim 1,
   wherein, in the stitch imaging, when the plurality of radiation imaging units is housed in a plurality of housing units housing the plurality of radiation imaging units in an order of a first radiation imaging unit, a second radiation imaging unit, and a third radiation imaging unit, the display control unit displays on a display unit in an order of a first region, a second region, and a third region, a state of the first radiation imaging unit in the first region, a state of the second radiation imaging unit in the second region, and a state of the third radiation imaging unit in the third region.

4. The information processing apparatus according to claim 1, wherein, in a case where at least one of the radiographic imaging unit is not connected communicatively with the information processing apparatus, the display control unit displays on a display unit that the at least one of the plurality of radiographic imaging unit is not connected communicatively with the information processing apparatus.

5. The information processing apparatus according to claim 1,
wherein the display control unit displays a radio wave state of each of the plurality of radiographic imaging units on a display unit.

6. The information processing apparatus according to claim 1, wherein the display control unit displays on a display unit that an error has occurred in at least one of the plurality of radiation imaging units.

7. The information processing apparatus according claim 1, wherein when an error occurs in the plurality of radiation imaging units, the display control unit displays on a display unit that an error has occurred in each of the plurality of radiation imaging units.

8. The information processing apparatus according to claim 1,
wherein the display control unit displays the state information acquired from the plurality of radiographic imaging units on a display of the display unit.

9. The information processing apparatus according to claim 1,
wherein the display control unit displays a connection state between the radiographic imaging unit and the information processing apparatus on the display unit.

10. The information processing apparatus according to claim 1,
wherein the display control unit displays battery states of the plurality of radiographic imaging units on the display unit.

11. The information processing apparatus according to claim 1,
wherein the display control unit displays radio wave states of wireless communication of the plurality of radiographic imaging units on the display unit.

12. An information processing method of an information processing apparatus configured to connect communicatively with a plurality of radiographic imaging units for stitch imaging, the information processing method comprising:
controlling a display control unit to individually display, for each of the plurality of radiographic imaging units, information which indicates whether or not the each of the plurality of radiographic imaging unit is in a state prepared for generating an image.

13. A non-transitory computer-readable storage medium storing a program for causing a computer to perform the information processing method according to claim 12.

14. An information processing apparatus configured to connect communicatively with a plurality of radiographic imaging units for stitch imaging, the information processing apparatus comprising:
a memory storing a program; and
one or more processors which, by executing the program, function as:
a display control unit configured to display, in a case where the radiographic imaging unit is not connected to the information processing apparatus, on a display unit that at least one of the plurality of radiographic imaging unit is not connected communicatively with the information processing apparatus.

15. An information processing method for controlling stitch imaging using a plurality of radiographic imaging units connectable to an information processing apparatus, the information processing method comprising:
controlling a display control unit to display, in a case where the at least one of the plurality of radiographic imaging unit is not connected communicatively with the information processing apparatus for stitch imaging, on the display unit that the radiographic imaging unit is not connected to the information processing apparatus.

16. A non-transitory computer-readable storage medium storing a program for causing a computer to perform the information processing method according to claim 15.

17. An information processing apparatus configured to connect via radio waves to a plurality of radiographic imaging units, the information processing apparatus comprising:
a memory storing a program; and
one or more processors which, by executing the program, function as:
a display control unit configured to display a radio wave state of each of the plurality of radiographic imaging units on a display unit.

18. An information processing apparatus configured to connect communicatively with a plurality of radiographic imaging units for stitch imaging using a plurality of radiographic imaging units, the information processing apparatus comprising:
a memory storing a program; and
one or more processors which, by executing the program, function as:
a display control unit configured to display on a display unit that an error has occurred in at least one of the plurality of radiation imaging units.

* * * * *